(12) United States Patent
Roblin et al.

(10) Patent No.: US 8,518,236 B2
(45) Date of Patent: Aug. 27, 2013

(54) ELECTRODE PRECONDITIONING

(75) Inventors: Patricia Mary Elizabeth Roblin, Yarnton (GB); Mark Hyland, Yarnton (GB); Christopher Paul Newman, Yarnton (GB)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 814 days.

(21) Appl. No.: 11/993,418

(22) PCT Filed: Jun. 28, 2006

(86) PCT No.: PCT/GB2006/002373
§ 371 (c)(1),
(2), (4) Date: Dec. 20, 2007

(87) PCT Pub. No.: WO2007/000596
PCT Pub. Date: Jan. 4, 2007

(65) Prior Publication Data
US 2010/0140108 A1    Jun. 10, 2010

Related U.S. Application Data

(60) Provisional application No. 60/695,157, filed on Jun. 29, 2005.

(51) Int. Cl.
*G01N 27/327* (2006.01)
*G01N 27/403* (2006.01)
(52) U.S. Cl.
USPC ............... 205/775.5; 205/792; 204/157.61; 204/434; 204/406

(58) Field of Classification Search
USPC ............... 204/280–296, 403.01–403.15, 402, 204/157.61, 406, 434; 205/777.5, 778, 792, 205/775; 422/68.1–98
See application file for complete search history.

(56) References Cited

U.S. PATENT DOCUMENTS

| | | | |
|---|---|---|---|
| 5,185,256 A | | 2/1993 | Nankai et al. |
| 5,288,636 A | * | 2/1994 | Pollmann et al. ......... 204/403.14 |
| 5,324,400 A | * | 6/1994 | Eliash et al. .................. 205/794 |
| 5,525,511 A | * | 6/1996 | D'Costa ................... 204/403.09 |
| 5,653,863 A | * | 8/1997 | Genshaw et al. ........... 205/777.5 |
| 6,270,637 B1 | * | 8/2001 | Crismore et al. ......... 204/403.04 |

(Continued)

FOREIGN PATENT DOCUMENTS

| | | |
|---|---|---|
| GB | 0414546.2 | 9/2005 |
| GB | 0611800.4 | 6/2006 |

(Continued)

OTHER PUBLICATIONS

Chen et al. (Electroanalysis 2001, 13, No. 1, pp. 61-67).*

(Continued)

*Primary Examiner* — J. Christopher Ball
*Assistant Examiner* — Jennifer Dieterle
(74) *Attorney, Agent, or Firm* — Quarles & Brady LLP; George E. Haas

(57) ABSTRACT

A method for improving the precision of electrochemical measurements made using an electrochemical cell is provided. The method comprises preconditioning a working electrode of the cell by (i) baking the working electrode; and/or (ii) incubating the working electrode; and/or (iii) applying a preconditioning potential across the cell; and/or (iv) treating the working electrode with a UV laser.

24 Claims, 15 Drawing Sheets

(56) References Cited

U.S. PATENT DOCUMENTS

| | | | |
|---|---|---|---|
| 6,280,604 B1* | 8/2001 | Allen et al. | 205/777.5 |
| 6,592,730 B1* | 7/2003 | Kelsch et al. | 204/412 |
| 2002/0026110 A1 | 2/2002 | Parris et al. | |
| 2003/0042150 A1* | 3/2003 | Ryu et al. | 205/778 |
| 2004/0131100 A1* | 7/2004 | Bragin et al. | 372/55 |
| 2005/0230252 A1* | 10/2005 | Tsai et al. | 204/450 |
| 2005/0284773 A1* | 12/2005 | Allen | 205/777.5 |
| 2006/0201805 A1* | 9/2006 | Forrow et al. | 204/403.1 |

FOREIGN PATENT DOCUMENTS

| | | |
|---|---|---|
| WO | WO 03/056319 | 7/2003 |
| WO | WO 2006/000827 | 1/2006 |
| WO | WO 2006/000828 | 1/2006 |

OTHER PUBLICATIONS

Stulik, Electroanalysis, 4, 1992, pp. 829-834.*
Blaedel et al. (Analytical Chemistry, vol. 47, No. 8, Jul. 1975, 1337-1343).*
Engstrom (Anal. Chem., 1982, 54, 2310-2314).*
International Search Report corresponding to PCT/GB2006/002373 under date of mailing of Nov. 28, 2006.
Netchiporouk L I, et al.: "Properties of carbon fibre microelectrodes as a basis for enzyme biosensors"; Analytica Chimica Acta, Elsevier, Amsterdam, NL; vol. 303, No. 2-3, 1995, pp. 275-283; XP002360927; ISSN: 0003-2670; p. 277.
Csorgi E, et al.: "Carbon fibers as electrode materials for the construction of peroxidase-modified amperometric biosensors"; Analytica Chimica Acta, Elsevier, Amsterdam, NL; vol. 273, No. 1/2, Feb. 15, 1993; pp. 59-70; XP002083874; ISSN; 0003-2670; p. 61-62.
Nam, et al.: "Effect of pre-treatment on the surface and electrochemical properties of screen-printed carbon paste electrodes"; Analyst; vol. 126, 2001, pp. 1399-1403.
Wang, et al : "Electrochemical activation of screen-printed carbon strips"; vol. 121, 1996; pp. 345-350.
Online extract from www.epsilon-web.net, accessed Jun. 22, 2005.
Stulik, et al., "The Effect of Pulsed Laser Irradiation on the Properties of Glassy Carbon Electrodes," J. Electroanal. Chem. 250 (1988), pp. 173-181, Elsevier Sequoia S.A., Lausanne, The Netherlands.
Sternitzke, et al., "In Situ Laser Activation of Glassy Carbon Electrochemical Detectors for Liquid Chromatography: Demonstration of Improved Reversibility and Detection Limits," Analytical Chemistry, vol. 61, No. 17, Sep. 1, 1989, p. 1989-1993, American Chemical Society.
Hershenhart, et al., "In Situ Cleaning and Activation of Solid Electrode Surfaces by Pulsed Laser Light," Analytical Chemistry, vol. 56, No. 12, Oct. 1984, pp. 2256-2257, American Chemical Society.
Poon, et al., "Repetitive in Situ Renewal and Activation of Carbon and Platinum Electrodes: Applications to Pulse Voltammetry," Analytical Chemistry, vol. 59, No. 13, Jul. 1, 1987, pp. 1615-1620, American Chemical Society.
Poon, et al., "In Situ Laser Activation of Glassy Carbon Electrodes," Analytical Chemistry, vol. 58, No. 13, Nov. 1986, pp. 2745-2750, American Chemical Society.

* cited by examiner

ELECTRODE PRECONDITIONING

CROSS REFERENCE TO RELATED APPLICATIONS

This application represents the national stage application of International Application PCT/GB2006/002373, filed 28 Jun. 2006, which claims the benefit of U.S. Provisional Patent Application 60/695,157 filed 29 Jun. 2005, which is incorporated herein by reference in its entirety for all purposes.

FIELD OF THE INVENTION

The present invention relates to a method of preparing an electrochemical device and a device obtained or obtainable by such a method. In particular, the present invention relates to a method for improving the precision of measurements made using an electrochemical device.

BACKGROUND TO THE INVENTION

Electrochemical measurements are a convenient technique by which to determine the concentration of one or more analytes in a given sample. Devices have been described which enable electrochemical tests to be carried out very simply and quickly and which provide an almost immediate result. An example of such a device is that described in WO 03/056319. The electrochemical device described in this document employs a microelectrode, which helps to provide extremely rapid results and also to minimise the required sample volume. Such devices are therefore useful in the medical field where low sample volume is a key requirement.

However, a disadvantage of electrochemical devices described to date is the low precision of the measured result. This can be a particular problem in the medical field where precision and reproducibility of results are of paramount importance. New electrochemical methods and devices are therefore required which provide a higher degree of precision.

SUMMARY OF THE INVENTION

The present invention therefore provides a method of improving the precision and/or accuracy of measurements made using an electrochemical cell. The method of the invention comprises preconditioning the working electrode of an electrochemical cell by (i) baking the working electrode; and/or (ii) incubating the working electrode; and/or (iii) applying a preconditioning potential across the cell; and/or (iv) treating the working electrode with a UV laser. An electrochemical measurement may then be carried out using the thus preconditioned cell.

In a particular embodiment, the invention provides a method of preparing an electrochemical sensing device comprising preconditioning the working electrode of an electrochemical cell as set out above. The method typically comprises
(a) providing an electrochemical cell having a working electrode and a pseudo reference electrode;
(b) preconditioning the working electrode by (i) baking the working electrode; and/or (ii) incubating the working electrode; and/or (iii) applying a preconditioning potential across the cell; and/or (iv) treating the working electrode with a UV laser; and
(c) providing an electroactive reagent to the electrochemical cell and optionally drying the reagent.

In one embodiment, the method further comprises
(d) supplying a sample to the device, the sample being in contact with the working electrode and with the electroactive reagent; and
(e) applying a measuring potential across the cell and measuring the resulting electrochemical response.

One or more of preconditioning steps (i) to (iv) may be employed. The or each step may be carried out either before or after provision of an electroactive reagent in step (c). Typically, baking and incubating are carried out either before step (c) or between steps (c) and (d). Typically, the electrochemical preconditioning step (iii) is carried out either before step (c), between steps (c) and (d) or between steps (d) and (e). Typically, laser treatment is carried out before step (c).

The present inventors have surprisingly found that preconditioning the working electrode prior to electrochemical measurement provides greater precision and a lower statistical dispersion in any electrochemical measurement which is subsequently carried out. Therefore, in the context of the present invention, improving the precision of electrochemical measurements made using an electrochemical cell means that measurements made using the cell (which has been preconditioned in accordance with the invention) have a lower statistical dispersion compared with equivalent measurements made on an identical cell which has not been preconditioned. For example, the coefficient of variation of an electrochemical measurement may be reduced.

The present invention also provides an electrochemical device which is obtained or obtainable by the method of the invention. The device typically comprises
an electrochemical cell having a working electrode and a pseudo reference electrode;
an electroactive reagent comprising an electrochemical mediator;
a potentiostat for applying a potential between the working and pseudo reference electrodes;
a controller for controlling the potentiostat; and
means for measuring the electrochemical response of the cell;
wherein the working electrode is a preconditioned electrode obtained by subjecting the working electrode to (i) baking; and/or (ii) incubating; and/or (iii) a preconditioning potential; and/or (iv) UV laser treatment.

In an alternative embodiment, the device of the invention comprises
an electrochemical cell having a working electrode and a pseudo reference electrode;
an electroactive reagent comprising an electrochemical mediator;
a potentiostat for applying a potential between the working and pseudo reference electrodes;
a controller for controlling the potentiostat so that firstly a preconditioning potential is applied and subsequently a measuring potential is applied; and
means for measuring the electrochemical response of the cell.

Also provided is an electrochemical sensing method comprising providing a sample to an electrochemical device according to the invention, applying a potential across the electrochemical cell and measuring the resulting electrochemical response.

Also provided is the use of an electrode preconditioning step in improving the precision of electrochemical measurements made using an electrochemical cell, the preconditioning step comprising (i) baking the working electrode; and/or (ii) incubating the working electrode; and/or (iii) applying a preconditioning potential across the cell; and/or (iv) treating the working electrode with a UV laser.

DETAILED DESCRIPTION OF THE INVENTION

Figure 1:
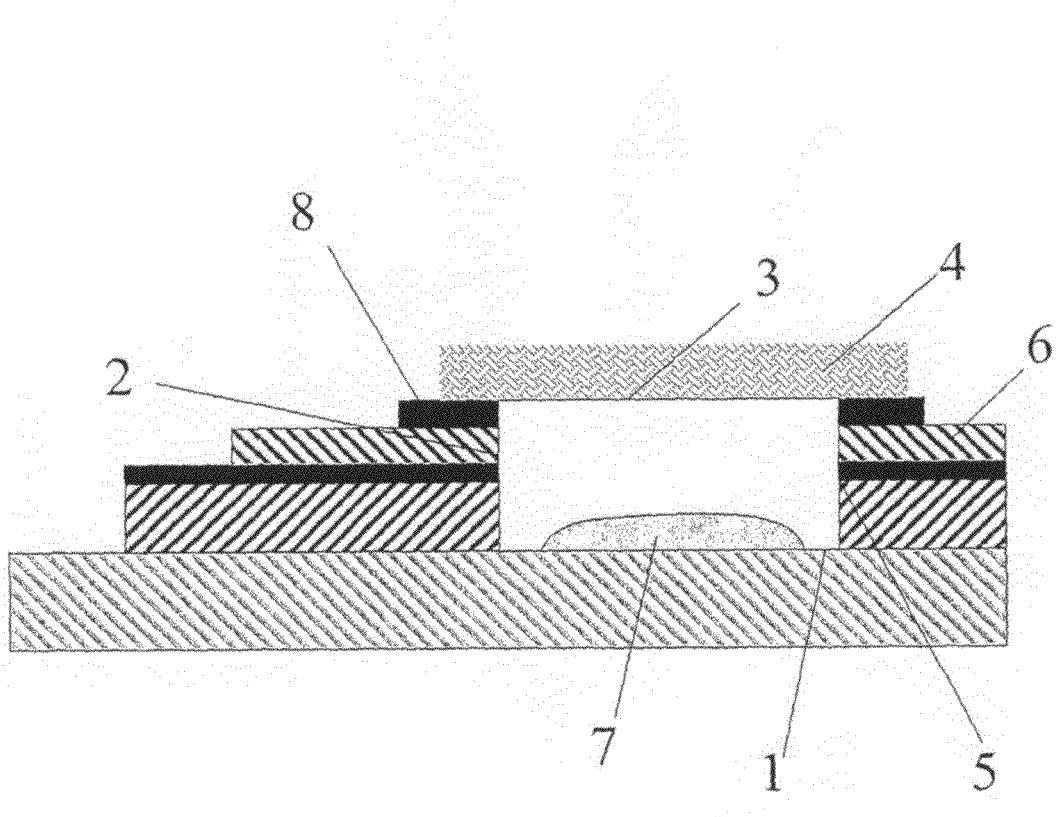
FIG. 1 depicts a device according to one embodiment of the invention.

The method of the present invention involves preconditioning the working electrode by (i) baking the working electrode; and/or (ii) incubating the working electrode; and/or (iii) applying a preconditioning potential across the cell; and/or (iv) treating the working electrode with a UV laser. One or more of the preconditioning methods (i) to (iv) may be used, for example a pre-conditioning potential may be used alone, or application of a preconditioning potential may be combined with baking and/or incubating. In an alternative embodiment, the preconditioning step comprises baking and/or incubating the electrode. Alternatively, laser treatment may be combined with one or more of baking, incubating and/or electrochemical pre-treatment. The preconditioning step may be carried out at any stage in the process for manufacturing the electrochemical device, as long as it is carried out after formation of the working electrode. Thus, further manufacturing steps may be completed after electrode preconditioning. Alternatively, preconditioning is carried out after the device has been manufactured.

In one embodiment of the invention, the preconditioning step comprises baking the working electrode. This is typically achieved by placing a device comprising the working electrode in an oven and heating at a temperature of up to 150° C., for example from 20 to 50° C., or alternatively from 70 to 130° C. The maximum heating temperature may, however, vary depending on the substrate and heating technique used. Baking may be carried out in the presence of light, or in the dark. Baking is typically carried out for at least 1 minute or at least 10 minutes, for example at least 3 hours. The maximum baking time is typically 48 hours, for example 10 hours or 6 hours. Oven heating, forced air drying and a heating are examples of suitable heating techniques. Preferred baking conditions are at about 130° C. for about 30 minutes or at about 100° C. for about 2 hours.

Baking may be carried out in air, or alternatively in the presence of a reactive or non-reactive assist gas. A suitable reactive assist gas is oxygen. Suitable non-reactive assist gases include inert gases e.g. argon, and nitrogen. A dessicant may also be present during baking, e.g. silica gel and/or another known dessicant. Molecular sieves may be used as the dessicant.

In an alternative embodiment, the preconditioning step comprises incubating the working electrode. This is typically achieved by exposing the working electrode to air, a reactive assist gas (e.g. oxygen) or a non-reactive assist gas (e.g. nitrogen, inert gases, argon) for from 1 to 30 days, e.g. for at least 2, 3, 4, 5, 10 or 12 days, for example for no more than 8, 10, 12, 15, 20 or 25 days. Incubation is typically carried out at between −25° C. and 30° C., for example from 0 to 25° C., e.g. 10 to 25° C. or about room temperature (18 to 25° C.). Incubating at above about 30° C. tends to reduce or negate any improvement in sensor response. Incubation may also be carried out either in the dark or in the presence of light and optionally in the presence of a dessicant such as those mentioned above. The presence of a desiccant during incubation leads to improved precision in sensor results.

Incubation is preferably carried out at a humidity of 70% or less, for example 50% or less, or 25% or less. This has been shown to lead to improved sensor precision.

In a further embodiment, the method of the invention involves preconditioning the working electrode by applying a preconditioning potential across the cell, between the working electrode and another electrode (typically a counter or pseudo reference electrode). The preconditioning potential may be applied, for example, by scanning or stepping the potential. Where a scan is used, the scan rate is typically from 10 $mVs^{-1}$ to $10Vs^{-1}$, for example at least 50 $mVs^{-1}$, 100 $mVs^{-1}$, 200 $mVs^{-1}$ or 500 $mVs^{-1}$. The maximum scan rate is, for example $5Vs^{-1}$, $2Vs^{-1}$ or $1Vs^{-1}$. The scan is typically carried out by sweeping the potential between a lower limit which is typically −1V or a less negative potential and an upper limit which is typically +1.8V or less. One or more potential sweeps may be carried out. The scan may be carried out from a lower to a higher potential or vice versa. A triangular sweep between two limits is also envisaged.

Where the preconditioning potential is stepped rather than scanned, the potential step applied is typically in the range of −1V to +1.8V. The potential may be applied for a duration of from 0.1 to 1000 s, for example from 1 to 300 s or from 1 to 100 s. One or more potential steps, employing the same or different potentials, may be used.

As used herein, all voltages are quoted in accordance with the IUPAC convention and against a Ag/AgCl reference electrode.

In one embodiment of the invention, electrochemical preconditioning is carried out in the presence of an aqueous solution which contacts the working and pseudo reference electrodes of the cell. In this embodiment, the electrochemical preconditioning step is typically carried out before supplying an electroactive reagent to the cell. The presence of an aqueous solution allows current to pass between the electrodes. Alternative materials capable of allowing a current to pass may be used if desired. Typically, the aqueous solution is a buffer having a pH of from 5 to 9. The aqueous solution typically does not contain a material which is electrochemically active at the preconditioning potentials employed. Preferably the aqueous solution comprises an electrolyte.

Suitable aqueous solutions include one or a mixture of solutions selected from (a) physiological saline solutions, (b) peroxide solutions and (c) solutions containing anions which can be activated to form per-derivatives. The physiological saline solutions include Tyrode's solution, Ringer's solution and Locke's solution and other solutions known in the art. Tyrode's solution, for example, comprises NaCl, KCl, $CaCl_2.6H_2O$, $MgCl_2.6H_2O$, $NaHCO_3$, $NaH_2PO_4$, glucose and distilled water.

Examples of suitable peroxides include hydrogen peroxide. Examples of anions which can be activated to form per-derivatives include carbonate, which can be activated to percarbonate, sulphate which can be activated to persulphate and borate which can be activated to perborate. Such activation typically occurs on application of an oxidising potential.

Pre-treatment may also be carried out by completing a first electrochemical pre-treatment step in the presence of a first solution, and a second (and optionally further) pre-treatment steps in the presence of the same or a different solution. A particularly improved sensor result is achieved when a first pre-conditioning potential is applied in the presence of a physiological saline solution and a second pre-conditioning potential is applied in the presence of an anion which can be activated to form a per-derivative, indicating that a synergy is occurring.

In an alternative embodiment, the electrochemical preconditioning step is carried out after an electroactive reagent is supplied to the cell. Alternatively, electrochemical preconditioning may be carried out after a sample has been provided to the device. In this embodiment, the electroactive reagent, or optionally the sample, allows current to pass between the electrodes. A further aqueous solution is not therefore required.

In the case of applying a preconditioning potential after the sample is provided to the device, the preconditioning potential is typically applied at an early stage, e.g. before completion of any reaction between the sample and the electroactive reagent. Thus, for example, the preconditioning potential may be applied after the sample has contacted the electrodes, but before contact occurs between the reagent and the sample. Alternatively, the preconditioning potential may be applied after the reagent and sample contact one another. For example, if the reagent is in dried form, the preconditioning potential may be applied whilst the reagent is being re-suspended in the sample. Typically, in this embodiment, the preconditioning potential is applied within about 2 minutes, for example within about 100 seconds of providing the sample.

In a preferred aspect of this embodiment, one or more potential steps is applied in order to precondition the electrode. For example, both a positive and a negative potential step may be applied. In this manner, any electrochemistry which occurs during the first potential step is typically reversed by application of the second potential step. This reduces any interference with a later electrochemical measurement. The potential steps applied are typically in the range of −1V to +1.8V, typically for a duration of from 0.1 to 1000 s, e.g. 0.1 to 100 s. A typical duration for application of a potential step is from 1 to 300 s.

In one embodiment of the invention, the preconditioning steps are not carried out in the presence of cobalt (including a cobalt salt or complex). Typically, the preconditioning steps are not carried out in the presence of a metal which is capable of adsorbing, or substantially adsorbing, to the working electrode.

In a further embodiment, the method of the invention involves treating the working electrode with a UV laser. Any laser operating in the UV range may be used, but appropriate wavelengths include from 50 to 400 nm, for example at least 10 nm or at least 150 nm. Pulsed or continuous wave lasers may be used, e.g. lasers with a pulse width of 0.1 ps to 1000 ps or from 0.1 ns to 1000 ns, e.g. 1 ns to 100 ns. Excimer lasers, vanadate lasers and YAG lasers, e.g. multiple (including double, triple and quadruple) frequency vanadate and YAG lasers, can be used.

Laser treatment is carried out by directing a laser-produced UV beam towards the electrodes. Treatment is preferably continued for at least 2 seconds, for example at least 3 seconds. This can conveniently be combined with the manufacture of the device as described below.

An electroactive reagent may be provided to the cell, either before or after preconditioning the electrode, and optionally dried. When a sample for testing enters the cell, it may react with the electroactive reagent and a measurable electrochemical response be produced.

The electroactive reagent is typically substantially free of, or does not contain, cobalt. Preferably, the electroactive reagent is substantially free of, or does not contain, a metal capable of adsorbing to the working electrode.

Typically, the electroactive reagent comprises an electrochemical mediator. An electrochemical mediator is a material having two or more oxidation states of distinct electroactive potentials so that it is capable of reversibly transferring electrons/charge between an electrode and another electrochemical couple. An electrochemical mediator is typically diffusive, i.e. it transfers electrons by diffusing through a liquid between the electrode and electrochemical couple. Suitable mediators are well known in the art and include ruthenium complexes (for example ruthenium (III) hexaamine salts) as well as ferricyanide or ferrocyanide salts. Phenylene diamines are also suitable mediators.

The electroactive reagent may also comprise a catalyst. Examples of catalysts are enzymes, for example lactate oxidase, cholesterol dehydrogenase, glycerol dehydrogenase, lactate dehydrogenase, glycerol kinase, glycerol-III-phosphate oxidase and cholesterol oxidase.

The electroactive reagent may optionally be dried into position in the electrochemical device, for example by air drying, oven drying, vacuum drying or freeze drying. The method of the present invention may be carried out on any device comprising an electrochemical cell. The electrochemical cell may be either a two-electrode or a three-electrode system. A two-electrode system comprises a working electrode and a pseudo reference electrode. A three-electrode system comprises a working electrode, a pseudo reference electrode and a separate counter electrode. As used herein, a pseudo reference electrode is an electrode that is capable of providing a reference potential. In a two-electrode system, the pseudo reference electrode also acts as the counter electrode and is thus able to pass a current without substantially perturbing the reference potential. In a three electrode system, the pseudo reference electrode typically acts as a true reference electrode and is, for example, a mercury/mercurous sulphate or calomel electrode.

In one embodiment of the invention, the electrochemical cell is in the form of a receptacle. The receptacle may be in any shape as long as it is capable of containing a liquid which is placed into it. For example, the receptacle may be cylindrical. Generally, a receptacle will contain a base and a wall or walls which surround the base. In this embodiment, the material comprising a transition metal salt is typically located in the receptacle.

It is preferred that the electrochemical cell has at least one microelectrode. Typically, the working electrode is a microelectrode. For the purposes of this invention, a microelectrode is an electrode having at least one dimension not exceeding 50 µm. The microelectrodes of the invention may have a dimension which is macro in size, i.e. which is greater than 50 µm.

A device according to one embodiment of the invention is depicted in FIG. 1. In this embodiment, the working electrode 5 is a microelectrode. The cell is in the form of a receptacle or a container having a base 1 and a wall or walls 2. Typically, the receptacle will have a depth (i.e. from top to base) of from 25 to 1000 µm. In one embodiment, the depth of the receptacle is from 50 to 500 µm, for example from 100 to 250 µm. In an alternative embodiment, the depth of the receptacle is from 50 to 1000 µm, preferably from 200 to 800 µm, for example from 300 to 600 µm. The length and width (i.e. from wall to wall), or in the case of a cylindrical receptacle the diameter, of the receptacle is typically from 0.1 to 5 mm, for example from 0.5 to 2.0 mm, e.g. 0.5 to 1.5 mm, such as 1 mm.

The open end of the receptacle 3 may be partially covered by an impermeable material as long as at least part of the open end is uncovered, or covered by a semi-permeable or permeable material, such as a semi-permeable or permeable membrane. Preferably, the open end of the receptacle is substantially covered with a semi-permeable or permeable membrane 4. The membrane 4 serves, inter alia, to prevent dust or other contaminants from entering the receptacle.

The membrane 4 is preferably made of a material through which the sample to be tested can pass. For example, if the sample is plasma, the membrane should be permeable to plasma. The membrane also preferably has a low protein binding capacity. Suitable materials for use as the membrane include polyester, cellulose nitrate, polycarbonate, polysulfone, microporous polyethersulfone films, PET, cotton and nylon woven fabrics, coated glass fibres and polyacrylonitrile fabrics. These fabrics may optionally undergo a hydrophilic or hydrophobic treatment prior to use. Other surface characteristics of the membrane may also be altered if desired. For example, treatments to modify the membrane's contact angle in water may be used in order to facilitate flow of the desired sample through the membrane. The membrane may comprise one, two or more layers of material, each of which may be the same or different, e.g. a composite of two or more membranes. For example, conventional double layer membranes comprising two layers of different membrane materials may be used.

The membrane may also be used to filter out some components which are not desired to enter the cell. For example, some blood products such as red blood cells or erythrocytes may be separated out in this manner such that these particles do not enter the cell. Suitable filtration membranes, including blood filtration membranes, are known in the art. Examples of blood filtration membranes are Presence 200 of Pall filtration, Whatman VF2, Whatman Cyclopore, Spectral NX, Spectral X and Pall BTS. Fibreglass filters, for example Whatman VF2, can separate plasma from whole blood and are suitable for use where a whole blood specimen is supplied to the device and the sample to be tested is plasma.

A spreading membrane may be used as an alternative to, or typically in addition to, a filtration membrane. Thus, for example, the membrane may be a composite of a spreading membrane and a filtration membrane, with the spreading membrane typically the outer membrane which will contact the specimen first. Appropriate spreading membranes are well known in the art and Petex is an example. In one embodiment, the membrane comprises a layer of a Petex membrane and a layer of a Pall BTS membrane.

The electrochemical cell of this embodiment of the invention contains a working electrode 5 which is situated in a wall of the receptacle. The working electrode is, for example, in the form of a continuous band around the wall(s) of the receptacle. The thickness of the working electrode is typically from 0.01 to 25 µm, preferably from 0.05 to 15 µm, for example 0.1 to 20 µm, more preferably from 0.1 to 10 µm. Thicker working electrodes are also envisaged, for example electrodes having a thickness of from 0.1 to 50 µm, preferably from 5 to 20 µM. The thickness of the working electrode is its dimension in a vertical direction when the receptacle is placed on its base. The area of the working electrode is typically no more than 5 mm$^2$, for example no more than 1 mm$^2$ or no more than 0.5 mm$^2$.

The working electrode is preferably formed from carbon, palladium, gold, platinum, silver or copper, for example in the form of a conductive ink. The conductive ink may be a modified ink containing additional materials, for example platinum and/or graphite. Two or more layers may be used to form the working electrode, the layers being formed of the same or different materials.

The cell also contains a pseudo reference electrode which may be present, for example, in the base of the receptacle, in a wall or walls of the receptacle or in an area of the device surrounding or close to the receptacle. The pseudo reference electrode is typically made from Ag/AgCl, although other materials may also be used. Suitable materials for use as the pseudo reference electrode will be known to the skilled person in the art. In this embodiment, the cell is a two-electrode system in which the pseudo reference electrode 8 acts as both counter and reference electrodes. Alternative embodiments in which a separate counter electrode is provided can also be envisaged.

The pseudo reference electrode typically has a surface area which is of a similar size to, or which is larger than, for example substantially larger than, that of the working electrode 5. Typically, the ratio of the surface area of the pseudo reference electrode to that of the working electrode is at least 1:1, for example at least 2:1 or at least 3:1. A preferred ratio is at least 4:1. The pseudo reference electrode may, for example, be a macroelectrode. Preferred pseudo reference electrodes have a dimension of 0.01 mm or greater, for example 0.1 mm or greater. This may be, for example, a diameter of 0.1 mm or greater. Typical areas of the pseudo reference electrode are from 0.001 mm$^2$ to 150 mm$^2$, e.g. up to 100 mm$^2$, preferably from 0.1 mm$^2$ to 60 mm$^2$, for example from 1 mm$^2$ to 50 mm$^2$. The minimum distance between the working electrode and the pseudo reference electrode is, for example from 10 to 1000 µm, for example from 10 to 300 µm or from 400 to 700 µm.

In order that the cell can operate, the electrodes must each be separated by an insulating material 6. The insulating material is typically a polymer, for example, an acrylate, polyurethane, PET, polyolefin, polyester, PVC or any other stable insulating material. Polycarbonate and other plastics and ceramics are also suitable insulating materials. The insulating layer may be formed by solvent evaporation from a polymer solution. Liquids which harden after application may also be used, for example varnishes. Alternatively, cross-linkable polymer solutions may be used which are, for example, cross-linked by exposure to heat or UV or by mixing together the active parts of a two-component cross-linkable system. Dielectric inks may also be used to form insulating layers where appropriate. In an alternative embodiment, an insulating layer is laminated, for example thermally laminated, to the device.

The electrodes of the electrochemical cell may be connected to any required measuring instruments by any suitable means. Typically, the electrodes will be connected to electrically conducting tracks which are, or can be, themselves connected to the required measuring instruments.

The electroactive reagent is typically contained within the receptacle, as depicted at 7 in FIG. 1. Typically, the reagent is inserted into the receptacle in liquid form and subsequently dried to help immobilise the composition. On introduction of a sample into the receptacle, the dried material is re-suspended forming a liquid comprising the reagent and the sample, the liquid being in contact with the working electrode which is located in the wall of the receptacle. The liquid is also typically in contact with the pseudo reference electrode. Thus, on application of a voltage across the cell, electrochemical reaction may occur and a measurable response (e.g. a current) be produced. Typically, a wet-up time, for example of one second, or from 1 to 60 seconds where a membrane is present over the receptacle, is provided before a voltage is applied, to allow the dried material to re-suspend.

The receptacle may, for example, contain one or more small air-holes in its base or its wall or walls (not depicted in FIG. 1). These holes allow air to escape from the receptacle when sample enters the receptacle. If such air-holes are not present, the sample may not enter the receptacle when it flows over the open end, or it may enter the receptacle only with difficulty. The air holes typically have capillary dimensions, for example, they may have an approximate diameter of 1-600 µm, for example from 100 to 500 µm. The air holes should be sufficiently small that the sample is substantially prevented from leaving the receptacle through the air holes due to surface tension. Typically, 1 or more, e.g. from 1 to 4 air holes may be present. In one embodiment, the base of the receptacle is formed by a porous hydrophilic or hydrophobic membrane, e.g. Versapor™ by Pall filtration. In this embodiment, air holes are provided by the pores in the membrane.

The cell may optionally comprise a separate counter electrode in addition to the working and pseudo reference electrodes. Suitable materials for producing the counter electrode will be known to the skilled person in the art. Ag/AgCl is an example of a suitable material.

Figure 2:
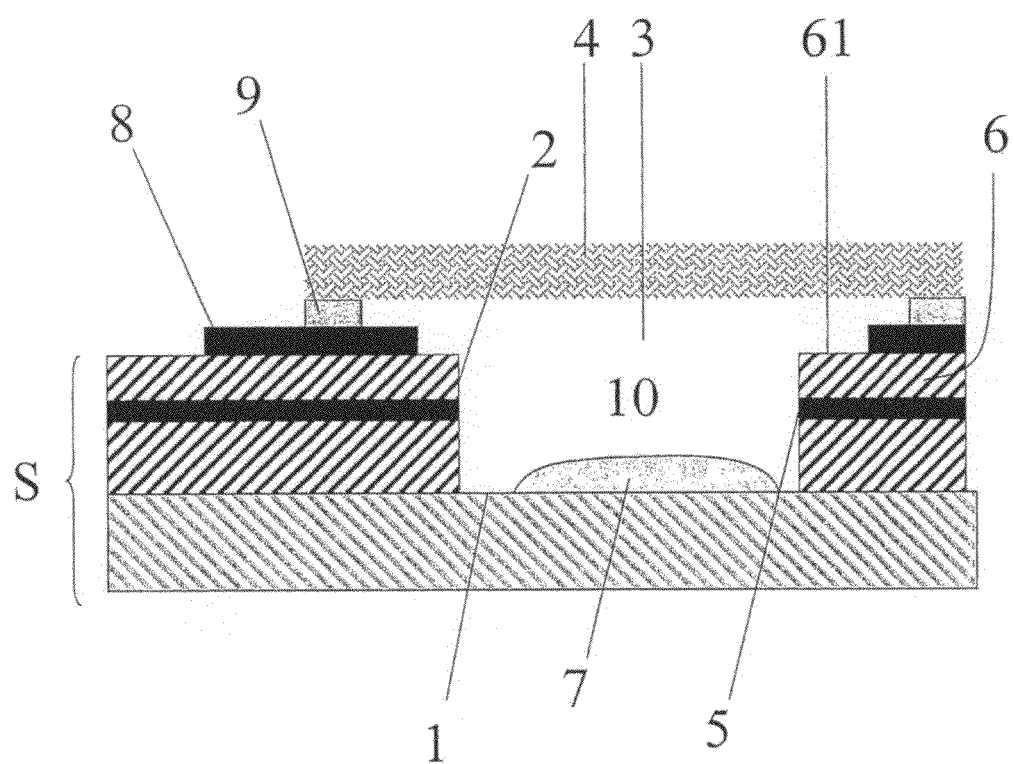
FIG. 2 depicts an alternative device according to the invention.

An alternative device according to the invention is depicted in FIG. 2. The device of this embodiment is the same as the device depicted in FIG. 1 and described above, except as set out below. In this embodiment, the device comprises a strip S. The strip S may have any shape and size, but typically has a first surface 61 which is substantially flat. The strip comprises a receptacle 10 bounded by base 1 and wall or walls 2. The device further comprises an electrochemical cell having a working electrode 5 in the wall(s) of the receptacle. The working electrode is typically a microelectrode.

The device of this embodiment comprises a pseudo reference electrode acting as reference electrode and optionally also as counter electrode. The pseudo reference electrode comprises a pseudo reference electrode layer 8 present on the first surface of the strip 61. The first surface of the strip is an external surface, i.e. it is a surface exposed to the outside of the device rather than a surface exposed to the interior of the receptacle. Typically, the pseudo reference electrode layer substantially surrounds the receptacle or partial receptacle 10. As depicted in FIG. 2, it is preferred that the pseudo reference electrode layer is not in contact with the perimeter of the first open part 3. Typically, the pseudo reference electrode layer is at a distance of at least 0.1 mm, preferably at least 0.2 mm from the perimeter of the first open part. At least a part of the pseudo reference electrode is, however, typically no more than 2 mm, for example no more than 1 mm or 0.5 mm, preferably no more than 0.4 mm from the perimeter of the first open part. In one embodiment, the pseudo reference electrode substantially surrounds the receptacle or partial receptacle at a distance of from 0.01 to 1.0 mm, for example from 0.1 to 0.5 mm, or 0.2 to 0.4 mm from the perimeter of the first open part. Alternatively, this distance may be from 0.01 to 0.3 mm or from 0.4 to 0.7 mm.

The thickness of the pseudo reference electrode is typically similar to or greater than the thickness of the working electrode. Suitable minimum thicknesses are 0.1 µm, for example 0.5, 1, 5 or 10 µm. Suitable maximum thicknesses are 50 µm, for example 20 or 15 µm.

The pseudo reference electrode 8 typically has a surface area which is of a similar size to, or which is larger than, for example substantially larger than, that of the working electrode 5. Typically, the ratio of the surface area of the pseudo reference electrode to that of the working electrode is at least 1:1, for example at least 2:1 or at least 3:1 preferably at least 4:1. The pseudo reference electrode may, for example, be a macroelectrode. Where the ratio of the surface area of the pseudo reference electrode to that of the working electrode is greater than 1:1, this helps to ensure that the electrochemical reaction occurring at the pseudo reference electrode is not current-limiting. The actual area of the pseudo reference electrode is, for example, from 0.001 mm$^2$ to 150 mm$^2$, e.g. up to 100 mm$^2$ or from 0.1 mm$^2$ to 60 mm$^2$, for example from 1 mm$^2$ to 50 mm$^2$.

A membrane 4 may be attached to the device by any suitable attachment means 9, for example using a double-sided adhesive tape. Typically, the attachment means attaches the membrane to the first surface of the strip or to the pseudo reference electrode layer. In a preferred embodiment as depicted in FIG. 2, the membrane is attached to the pseudo reference electrode layer 8 at a location which is remote from the perimeter of the receptacle itself. Further, the attachment means is at a greater distance from the first open part of the receptacle 3 than the pseudo reference electrode layer, such that at least a part of the surface of the pseudo reference electrode layer close to or surrounding the receptacle is exposed to a sample which has passed through the membrane. Preferably, the attachment means is at least 0.2 mm, for example at least 0.3 mm or at least 0.4 mm, from the perimeter of the receptacle.

In the embodiment depicted in FIG. 2, a reaction volume is defined by the receptacle base 1 and walls 2, part of the surface of the strip 61, the pseudo reference electrode layer 8, the attachment means 9 and the membrane 4. This reaction volume can be varied by changing the volume of the receptacle, the position and thickness of the pseudo reference electrode layer and the position and thickness of the attachment means 9. Preferred reaction volumes are at least 0.05 µl, for example at least 0.1 or at least 0.2 µl. It is further preferred that the reaction volume is no more than 25 preferably no more than 5 µl, for example no more than 3 µl or no more than 2 µl.

Further details regarding electrochemical devices which can be used in the present invention can be found in WO 03/056319 and WO 06/000828. The contents of these applications are incorporated herein by reference in their entirety.

The devices described above can be produced by forming a laminate structure comprising a layer of working electrode material (e.g. a layer of graphite) between two layers of insulating material. A hole is then created through this laminate, thus forming the wall(s) of the receptacle. A base, optionally comprising a pseudo reference electrode, may then be added. The pseudo reference electrode may alternatively be provided by printing a layer of a suitable material onto the surface of the laminate. Where one or more air holes are desired in the base or walks) of the receptacle, these can be formed by any suitable technique, for example by drilling or punching a hole, or by use of a porous membrane as the base. The electroactive reagent is inserted into the receptacle thus formed by any suitable technique, and typically dried.

Following insertion of the electroactive reagent, a membrane may be attached over the open end 3 of the receptacle. This can be achieved by any suitable means, for example by adhering the membrane to the top of the receptacle using double-sided adhesive.

Preconditioning of the working electrode is carried out after creation of the hole in the laminate. Preconditioning may, for example, be carried out before or after addition of the pseudo reference electrode layer, and before or after addition of the base. In the case of baking or incubating, preconditioning may also be carried out either before or after insertion of the electroactive reagent.

In the case of electrochemical preconditioning, if preconditioning is carried out before insertion of the electroactive reagent, an aqueous solution is typically provided in order to pass current between the electrodes. If electrochemical preconditioning is carried out after the electroactive reagent is provided to the cell, no separate aqueous solution is required. In this case, preconditioning is, for example, carried out during the wet-up time whilst the reagent is resuspending in the sample.

In the case of UV laser preconditioning, the preconditioning step can conveniently be combined with the step of forming the hole in the laminate. For example, the hole may be formed by laser drilling as described in WO 03/056319 and, following formation of the hole, application of the UV laser beam continued, for example for a further 2 seconds or more, in particular for a further 3 seconds or more.

Further details regarding the process for producing cells such as that depicted in FIGS. 1 and 2 can be obtained from WO 03/056319 and WO 06/000828.

Figure 3:
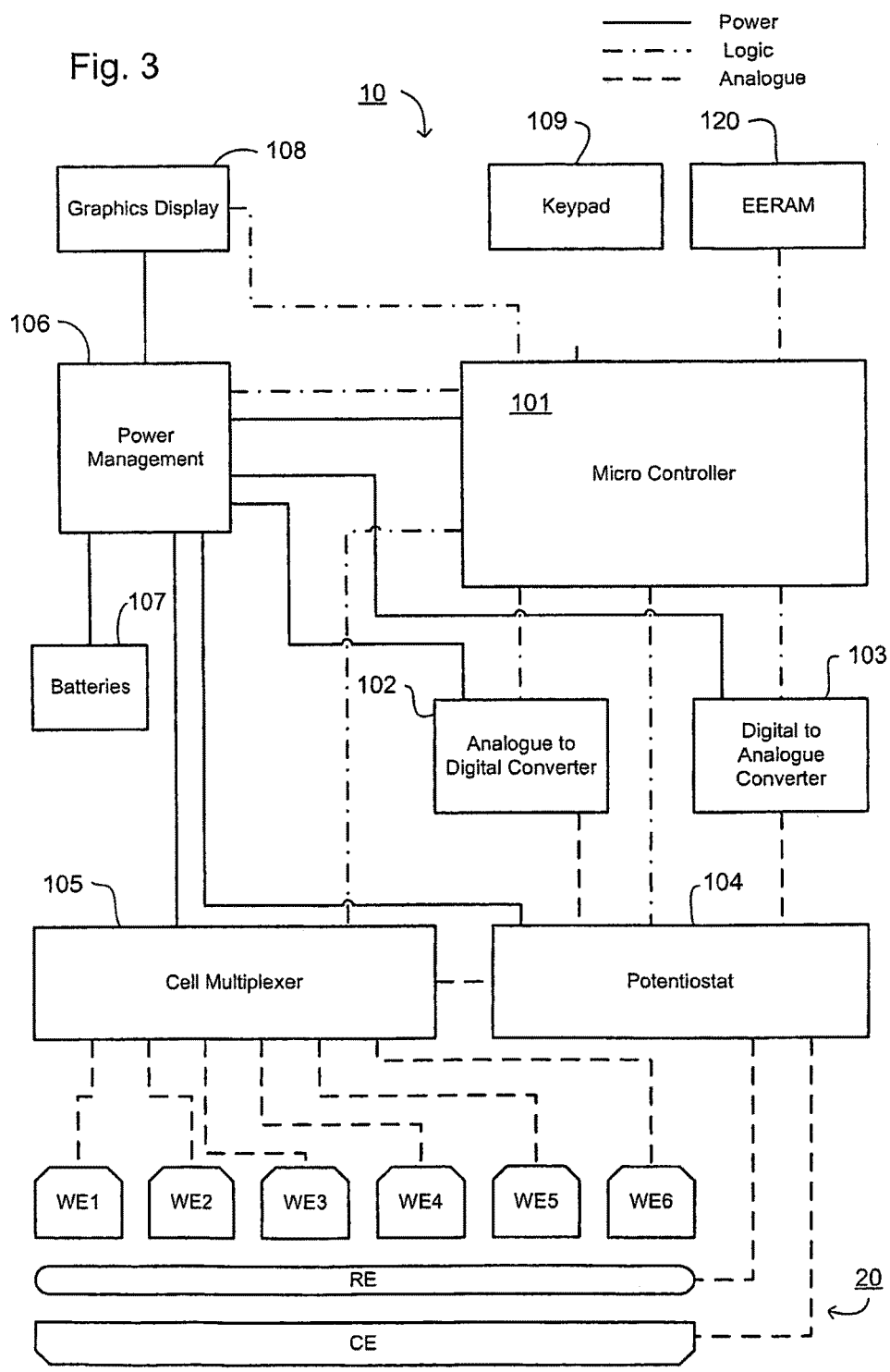
FIG. 3 is a schematic drawing of a portable electrochemical sensor device incorporating the invention.

A further aspect of the present invention is depicted in FIG. 3. This aspect of the invention may be incorporated into the devices described in the above embodiments.

In this aspect, the sensor device comprises an electronics unit 10 to which is connected an electrode unit 20, which may be disposable. The electrode unit 20 has a plurality of working electrodes WE1-WE6 as well as reference and counter (auxiliary) electrodes RE, CE. In some embodiments of the invention, the reference and counter electrodes may be combined as a single pseudo reference electrode. Different working electrodes WE1-WE6 may be adapted to carry out different electrochemical tests, if desired.

An electrochemical cell is formed between the working and counter (or pseudo reference) electrodes. To make measurements of a fluid that is in electrical connection with a working electrode, a measuring potential is applied between the working electrode and a reference/counter/pseudo reference electrode and the resulting current detected. The same or different measuring potentials can be applied between a reference/counter/pseudo reference electrode and each different working electrode.

Overall control of the electronics unit 10 of the sensor device is performed by a micro controller 101 which controls a potentiostat 104 via digital to analog converter 103 and receives measurement results from the potentiostat 102 via analog to digital converter 102. In one embodiment of the invention, the micro controller 101 is programmed to provide a preconditioning potential to the cell and subsequently to provide a measuring potential. The potentiostat 104 applies the desired voltages to the working, reference and counter electrodes WE, RE, CE; a cell multiplexer 105 under the control of microprocessor 101 selects the appropriate one of the working electrodes.

A graphics display 108 enables display of operating menus to the user, options being input via keypad 109, and measurement results. An electrically erasable RAM 120 allows for storage of both system software and measurement results. A bar code reader may also be provided for input of data, especially of patient information if the sensor is used in a medical or veterinary application. Interfaces, e.g. conforming to RS232, Bluetooth, Ethernet, USB, or WiFi (IEEE 802.11a, b, etc.) standards, may be provided for connection to printers, networks and other devices, e.g. patients records systems.

Power is supplied from batteries 107 under the control of a power management unit 106 that optimises battery life and controls recharging of the batteries.

The electrochemical device of the invention may be used in an electrochemical sensing method by supplying a sample for testing to the device, applying a potential across the cell and measuring the resulting electrochemical response. Typically, the resulting current is measured. The sample is typically a fluid (e.g. a liquid) or a gel. For example, the sample may be a sample of bodily fluid from a patient, e.g. blood or plasma.

The device may be used for determining the content of various substances in the sample. The device may, for example, be used to determine the pentachlorophenol content of a sample for environmental assessment; to measure cholesterol, HDL, LDL and triglyceride levels for use in analysing cardiac risk, or for measuring glucose levels, for example for use by diabetics. A further example of a suitable use for the device is as a renal monitor for measuring the condition of a patient suffering from kidney disease. In this case, the device could be used to measure the levels of creatinine, urea, potassium and sodium in the urine. The advantage of using the device of the invention in any of these tests is the increased precision of the results obtained.

EXAMPLES

In the experiments below, devices pretreated using a variety of techniques were analysed and the results of electrochemical tests to determine analyte concentrations were compared with known concentrations. The precision (% CV) of the readings for each sample was calculated using the formula:

$$\% \ CV = \frac{100 \times StDev}{Average}$$

StDev is the standard deviation of the results from a given sample, and average is the mean value.

Example 1

Heat Pre-Treatment

Electrochemical tests were carried out using devices of the type described in WO 2006/000828 (GB 0414546.2). The working electrode of the electrochemical cells was a carbon electrode and a Ag/AgCl pseudo reference electrode acting as both counter and reference electrodes was used.

Six devices were annealed at a temperature of 100° C. for 1, 2, 3, 4, 5, 6 and 7 hours respectively, in order to precondition the working electrode. In subsequent electrochemical testing, the highest degree of precision (lowest % CV), was observed for the devices annealed at from 3 to 7 hours, in particular at from 4 to 6 hours with the best result achieved at 4 hours annealing.

Example 2

Heat Pre-Treatment

Moisture analysis was, carried out on a number of heat pre-treated samples using a Sartorius moisture analyzer MA50H/16405485 having an IR halogen lamp as a heat source. For each experiment, 10 devices were tested, each device being of the type described in WO 2006/000828 and having been prepared by laser drilling the receptacle. The sample mass for each device is approximately 1.4 g.

Figure 4:
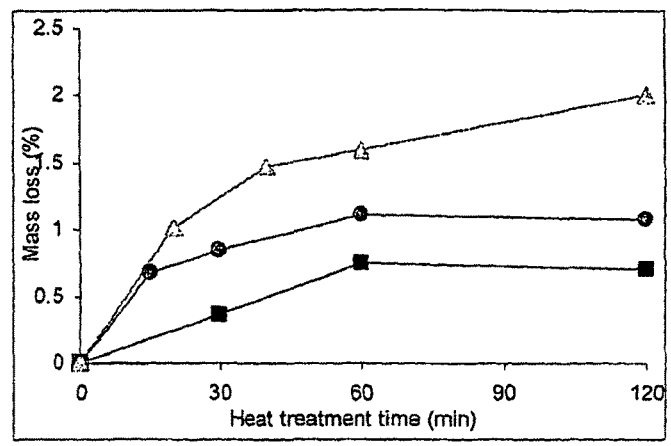
FIG. 4 shows the mass loss of a sensor during heat treatment at 100° C. (squares), 130° C. (circles) and 150° C. (triangles)

The final heating temperature was fixed at 100, 130 or 150 C. The heat treatment time was fixed at from 15 to 360 min. The released moisture was measured at 5 minute intervals. FIG. 4 shows the results in terms of mass loss over time for (a) heat treatment at 100° C. (squares), (b) heat treatment at 130° C. (circles) and (c) heat treatment at 150° C. (triangles).

Figure 5:
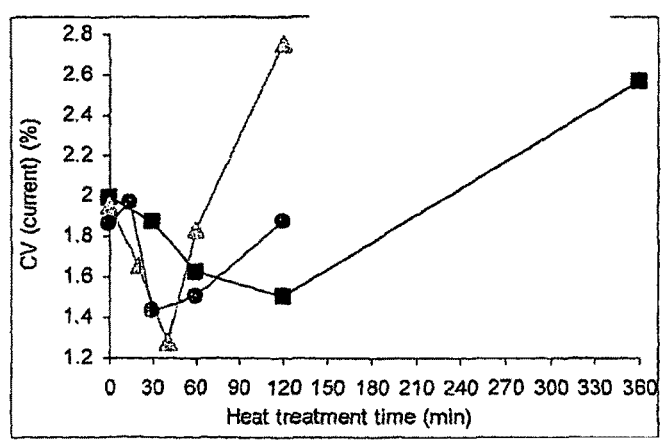
FIG. 5 shows the improvement in coefficient of variation (% CV) with respect to heat treatment times, following heat treatment at 100° C. (squares), 130° C. (circles) and 150° C. (triangles)
Figure 6:
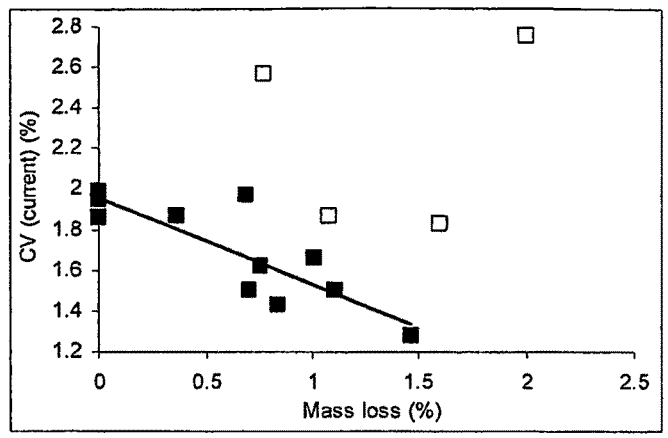
FIG. 6 shows the correlation of % CV with weight loss (filled squares show where the % CV decreases whereas opened squares show where the % CV increases)

The heat treated devices were then used in an electrochemical test in which the electrode was exposed to varying known mM concentrations of ruthenium hexaamine in 0.1 M buffer and a potential step of −0.45 V vs. AgAgCl applied. The concentration of ruthenium was determined electrochemically, compared with the known values and the coefficient of variation (CV) calculated. FIG. 5 shows the variation in measured CV vs time of heat treatment, wherein (a) squares depict devices heat treated at 100° C., (b) circles depict devices heat treated at 130° C. and (c) triangles depict devices heat treated at 150° C. As is apparent from FIG. 5, the heat treatment conditions can lead to large improvements in the observed electrochemical CV. A clear improvement in the reproducibility is observed at short heat treatment times. The CV reaches a minimum after an optimum baking time and then increases as the samples are heat treated for a longer time, most likely due to sensor cracking. This decrease in % CV appears correlated with weight loss, as depicted in FIG. 6. In FIG. 6, filled squares show a decreased CV, whereas open squares show an increased CV.

Example 3

Total Cholesterol Tests Using Heat Pre-Treated Devices

Devices of the type described in WO 2006/000828, each having four empty receptacles (i.e. containing no reagents) were placed in an oven pre-heated to 100° C. 12 to 13 sensors were removed at hourly intervals for a period of 7 hours and stored at room temperature. Total cholesterol assay solution was then manually dispensed into each receptacle (0.4 uL per receptacle). The assay solution used was as follows: 0.1M Tris (pH 9.0), 50 mM $MgSO_4$, 5% w/v glycine, 1% w/v myo-inositol, 1% w/v ectoine, 10% w/v sodium taurocholate, 80 mM $Ru(NH_3)_6Cl_3$, 8.8 mM thio-nicotinamide adenine dinucleotide (TNAD), 4.2 mg/mL Putidaredoxin reductase (PdR) 3.3 mg/mL cholesterol esterase (ChE) and 100 mg/mL cholesterol dehydrogenase (ChDH). The thus produced sensors were freeze dried overnight. The following morning, sensors were removed from the freeze dryer and Petex spreading membrane applied over each receptacle using double sided adhesive.

Figure 7:
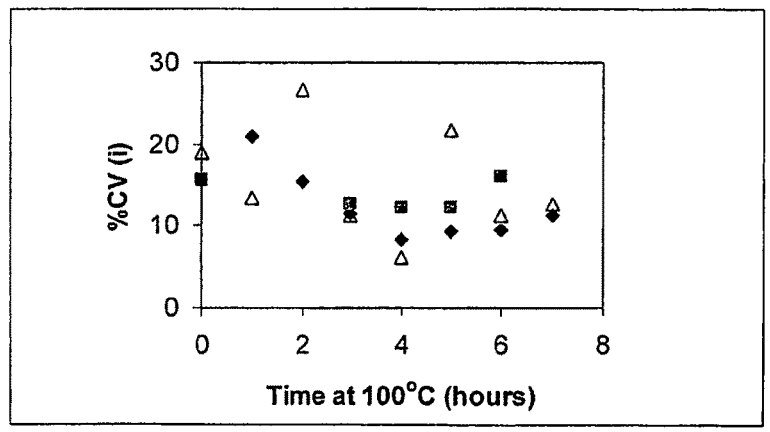
FIGS. 7 & 8 show the improvement in % CV with heat pre-treatment of electrodes of a total cholesterol sensor.
Figure 8:
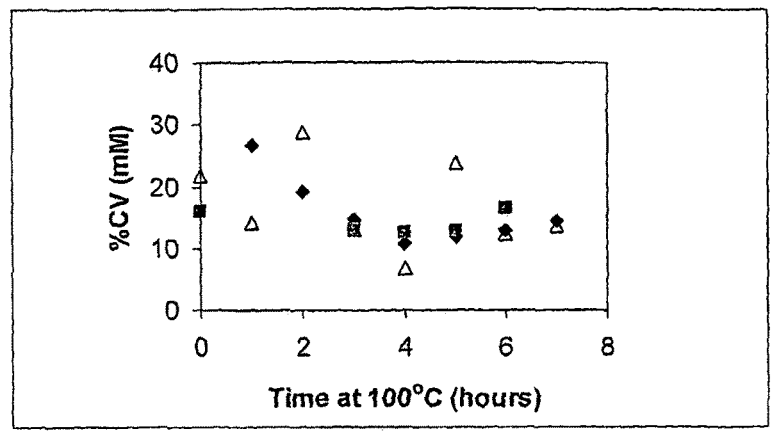

The sensor response of each sensor was tested using defrosted plasma samples with 3 levels of total cholesterol and delipidated serum from Scipac. The total cholesterol concentration of each sample was determined using a Space clinical analyser (Schiappanelli Biosystems Inc). Each sensor was tested by application of 5 uL plasma per sensor using a 20 uL Gilson pipette. Sensors were tested using a Princeton Applied Research Parstat 2263 instrument and a Sternhagen Design MX452 multiplexer. The delay time was 52 sec, followed by application of an oxidation potential of +150 mV vs. Ag/AgCl pseudo reference electrode for 1 second at each receptacle consecutively. The oxidation current was measured at the end of each current transient at 1 second, and the observed current values were plotted against total cholesterol concentration, for each set of sensors from each pre-treatment time. The line of best fit was determined and the average % CV was calculated based on current (% CV(i): FIG. 7) or analyte concentration (% CV(mM): FIG. 8). The experiment was repeated three times and the three results appear as squares, triangles and diamonds in FIGS. 7 and 8.

Example 4

Incubation

A device of the type depicted in WO 03/056319, having four electrochemical cells as depicted in WO 03/056319 wherein the base 1 is formed by a membrane (Pall Versapor) is used. The working electrode is a carbon electrode and the pseudo reference electrode is a Ag/AgCl electrode. A reagent mixture is inserted into each cell and freeze dried. The devices are then individually packaged with 4A molecular sieves as dessicant and stored at 20° C.

The reagent mixtures used are as follows. Batches of reagent mixture are made up in advance using the proportions specified below for either the total cholesterol or the triglyceride test.

Total Cholesterol Test (0.4 μl Inserted into the Electrochemical Cell)

0.1 M TRIS buffer, 0.05 M Magnesium sulphate ($MgSO_4$), 5% Glycine, 1% Inositol, 1% Ectoine, 5% CHAPS, 5% Deoxy bigCHAP, 80 mM Ruthenium (III) hexamine chloride ($Ru(NH_3)_6Cl_3$), 8.8 mM Thio-Nicotinamide adenine dinucleotide (TNAD), 4.1 mg/ml Putidaredoxin reductase (PDR), 3.3 mg/ml Cholesterol esterase (ChB), 66 mg/ml Cholesterol dehydrogenase (ChDH).

Triglyceride Test (0.4 μl Inserted into the Electrochemical Cell)

0.1 M HEPBS buffer, 0.01M Ammonium chloride ($NH_4Cl$), 10% Glycine, 1% Ectoine, 1% CHAPS, 80 mM Ruthenium (III) hexamine chloride ($Ru(NH_3)_6Cl_3$), 17.6 mM Thio-Nicotinamide adenine dinucleotide (TNAD), 6.5 mg/ml Diaphorase, 45 mg/ml Glycerol dehydrogenase, 100 mg/ml Lipase.

Experiments

A series of experiments were performed at intervals after the mixtures were freeze dried. Experiments took place at 0, 1, 5, 7, 10, 13 and 18 days according to the following protocol.

Samples

Lyophilised serum samples with known amounts of cholesterol and triglycerides were used. The samples were then analysed using a Space clinical analyser (Schiappanelli Biosystems Inc) and the concentrations recorded.

Testing Protocol

Figure 9:
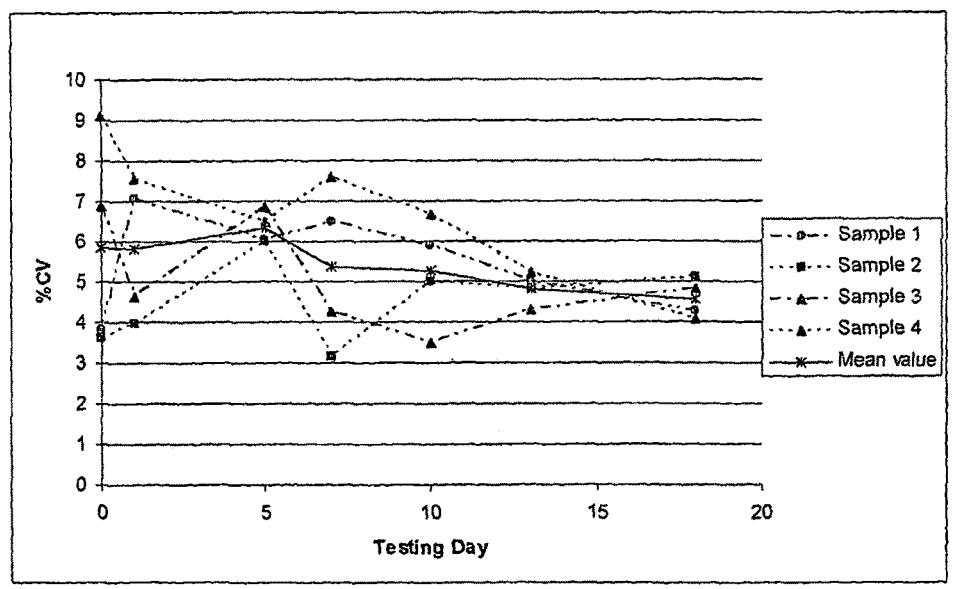
FIG. 9 shows the improvement in % CV with incubation time for total cholesterol sensors.
Figure 10:
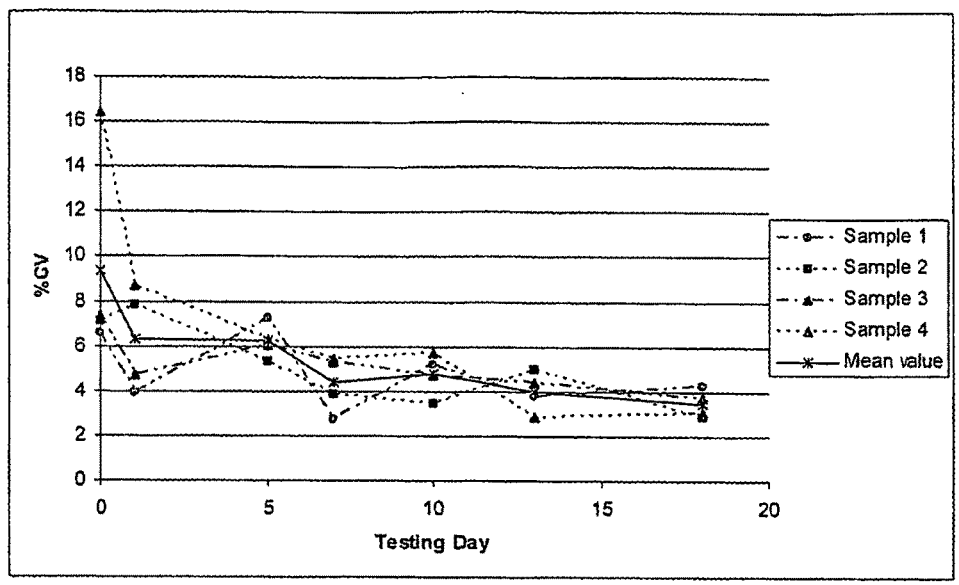
FIG. 10 shows the improvement in % CV with incubation time for triglyceride sensors.

5 μL of a sample were placed onto an electrode. At T=−14 seconds the chronoamperometry test was initiated using a multiplexer (MX452, Sternhagen Design) attached to an Autolab (PGSTAT 12) and GPES software v4.9.005. The oxidation current is measured at 0.15V at 11 time points (0, 14, 28, 42, 56, 70, 84, 98, 112, 126 and 140 seconds), with a reduction current measured at −0.45V at 141 seconds. Each sample was tested six times. The measured currents are used to generate total cholesterol or triglyceride concentrations, as relevant, and the % CV is determined as described above. The variation in % CV with incubation time is shown in FIG. 9 for total cholesterol tests and in FIG. 10 for triglyceride tests.

Example 5

Incubation and/or Baking

Devices of the type described in WO 2006/000828 each having four receptacles were used, with the following enzyme formulation inserted into each receptacle: 0.1M HUBS buffer (pH 9.0), 10 mM $NH_4Cl$, 10% w/v glycine, 1% w/v ectoine, 1% w/v sodium taurocholate (NaTC), 80 mM $Ru(NH_3)_6Cl_3$, 17.9 mM thio-nicotinamide adenine dinucleotide (TNAD), 6.6 mg/mL diaphorase, 45 mg/mL glycerol dehydrogenase and 100 mg/mL lipase. The enzyme mix was dispensed into the receptacles using a single head Allegro dispenser and freeze dried. All freeze dried sensors were stored in foil heat sealed bags with dessicant poggs until use. For each sensor, a 7×7 mm square of blood separation membrane (Pall BTS SP300) was attached over the receptacle using a single sided adhesive window (6×6 mm window).

Pre-Treatment of Sensors

Experiment 1

A row of sensors was removed from the foil bag, which was then resealed. A blood separation membrane from the Pall BTS range was applied to the sensors under laboratory temperature and humidity conditions. The sensors were then placed in a humidity chamber at 6 different pre-set temperature and humidity conditions as detailed in Table 1 for 30 minutes, prior to commencing testing as described below:

TABLE 1

|   | Temperature/° C. | % Humidity |
|---|---|---|
| 1 | 20 | 20 |
| 2 | 20 | 70 |
| 3 | 20 | 70 |
| 4 | 26 | 70 |
| 5 | 33 | 70 |
| 6 | 40 | 70 |

Testing of Sensors

The sensor response of each pre-treated set of sensors was tested using whole blood samples spiked with 3 levels of glycerol. A blank sample was prepared by centrifuging a whole blood sample, removing the plasma and replacing it with delipidated serum from Scipac. The triglyceride concentration of each sample was determined in advance of testing using a Space clinical analyser (Schiappanelli Biosystems Inc). The triglyceride concentration range was approximately 0-9 mM.

Each sensor was tested by application of 20 uL whole blood per sensor. A time period of 124 seconds was allowed to lapse after sample addition to allow mixing of sample with the enzyme formulation and to allow reaction to occur. An oxidation potential of +150 mV vs. Ag/AgCl pseudo reference electrode was then applied for 1.3 second at each receptacle consecutively.

Figure 11:
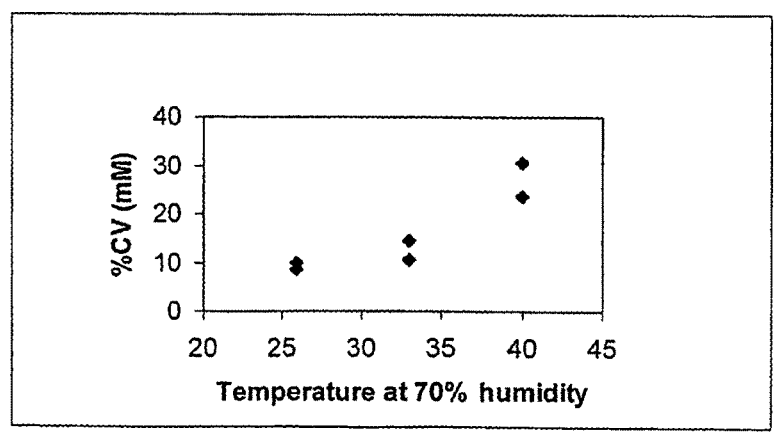
FIG. 11 demonstrates the increase in % CV with increasing temperature for sensors incubated at 70% humidity.
Figure 12:
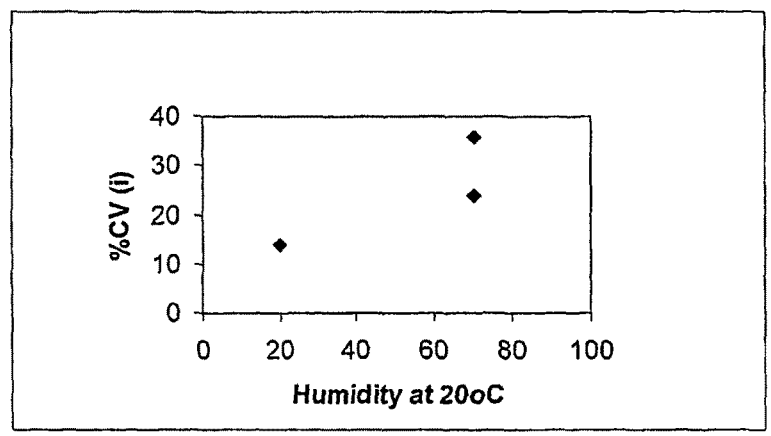
FIG. 12 demonstrates the increase % CV with increasing humidity for sensors incubated at 20° C.

The oxidation current was determined from the final 0.3 seconds of each current transient by averaging the current values during this period. The observed current values were plotted against triglyceride concentration, for each set of sensors from each set of experimental conditions. The line of best fit was determined and the average % CV was calculated based on analyte concentration. Results for conditions 4 to 6 of Table 1 are depicted in FIG. 11 (constant humidity, (% CV(mM)), whilst results for conditions 1 to 3 of Table 1 are depicted in FIG. 12 (constant temperature, (% CV(i)).

Pre-Treatment of Sensors

Experiment 2

Two rows of sensors were removed from the foil bag, which was then resealed. One row of sensors had a blood separation membrane from the Pall BTS range applied, and then both rows were exposed to 70% humidity at room temperature. The sensors were then placed in sealed foil bags with dessicant poggs for 48 hours. Membrane was applied to the set of sensors stored without membrane, and the sensor responses were determined according to the 'Testing of sensors' procedure given in Experiment 1 above. In addition, a control experiment was performed. A third row of sensors which had not been exposed to high humidity was removed from the foil bag, membrane applied and response to whole blood determined according to the 'Testing of sensors' procedure given in Experiment 1 above. All sensors were tested at 30% humidity and 26° C. The results of this Experiment are detailed in the following Table 2.

TABLE 2

| Experiment 2 | Best line fit | % CV (i) | % CV (mM) |
|---|---|---|---|
| Control | y = 51.687x + 161.77 | 14.0 | 20.7 |
| Membrane applied before exposure to high humidity | y = 52.125x + 123.83 | 23.7 | 27.2 |
| Membrane applied after exposure to high humidity | y = 49.357x + 97.971 | 35.7 | 62.8 |

Conclusions

Exposure of triglyceride sensors with freeze dried reagents to high humidity causes the reagents to absorb moisture. This causes loss of structure, and increases the dissolution time on addition of sample. Storage of freeze dried reagents, in a low humidity atmosphere after short exposure (30 minutes) to high humidity causes considerable increase in the scatter in response.

Example 6

Effect of Incubating in the Presence of a Dessicant

Devices as described in Example 4, and containing reagents for carrying out total cholesterol and triglyceride tests as described in Example 4 were used.

Experiments

A series of experiments were performed at intervals after the reagent mixtures were freeze dried. Storage of electrodes was at 30 C, 50% relative humidity and (a) in the presence of 4A molecular sieves as dessicant and (b) in the absence of a dessicant. Experiments took place at 0, 1, 12, 19 and 40 days according to the following protocol.

Samples

Lyophilised serum samples with known amounts of cholesterol and triglycerides were used. The samples were then analysed using a Space clinical analyser (Schiappanelli Biosystems Inc) and the concentrations recorded.

Testing Protocol

Figure 13:
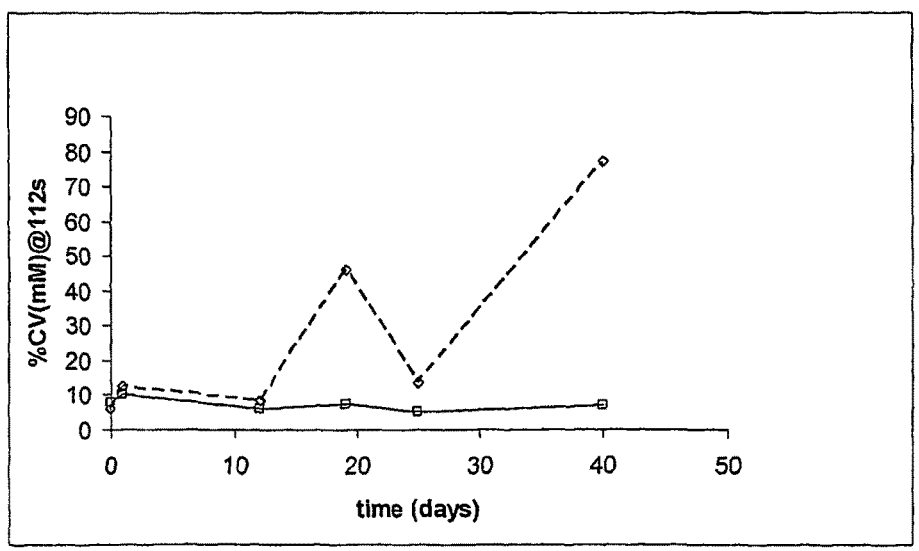
FIGS. 13 and 14 illustrate the effect of sensor incubation in the presence of a dessicant (solid line) and in the absence of a dessicant (dashed line)
Figure 14:
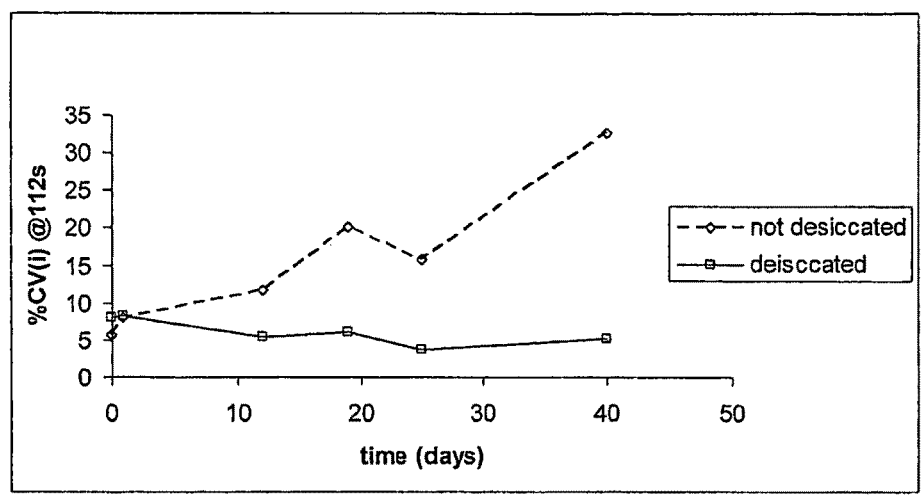

5 µL of a sample were placed onto an electrode. At T=−14 seconds the chronoamperometry test was initiated using a multiplexer (MX452, Stemhagen Design) attached to an Autolab (PGSTAT 12) and GPES software v4.9.005. The oxidation current was measured at 0.15V at 11 time points (0, 14, 28, 42, 56, 70, 84, 98, 112, 126 and 140 seconds), with a reduction current measured at −0.45V at 141 seconds. Each sample was tested eight times. The % CV vs storage time is depicted in FIGS. 13 (% CV (mM)) and 14 (% CV (i)) for dessicated samples (solid line) and non-dessicated samples (dashed line).

Example 7

Pretreatment Application of Potential Step

Figure 15:
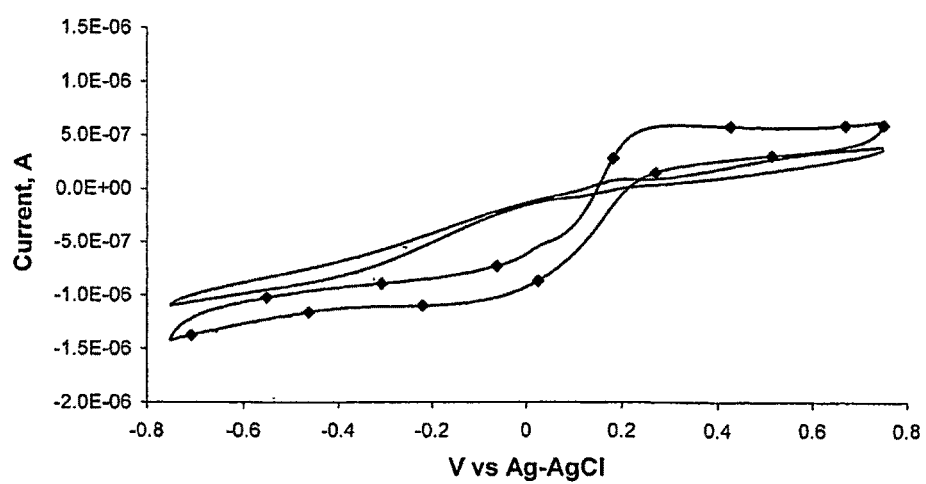
FIG. 15 shows the effect of application of a potential step prior to completing cyclic voltammetry, comparing voltammograms completed without pretreatment of electrodes (solid line) with those completed after pretreatment of electrodes (diamonds)

Cyclic voltammetry in the presence of ferricyanide solution was carried out (a) on a non-pre-treated electrochemical cell, and (b) on an identical electrochemical cell which had been pre-treated by application of a potential (+2.0 to +2.5 V vs Ag—AgCl) for a time of 10-60 seconds. Both pre-treatment and cyclic voltammetry were carried out in the presence of a ferricyanide solution consisting of 10 mM $K_3[Fe(CN)_6]$ (Aldrich) in Tris pH 9 buffer (Sigma) with 100 mM KCl (BDH), 50 mM $MgSO_4$ (Sigma) and 1% sodium taurocholate (Sigma). Cyclic voltammetry was performed at 100 mVs$^{-1}$. The results are depicted in FIG. 15.

Example 8

Electrochemical Pretreatment Using Tyrode's Solution or Sodium Carbonate

Tyrode's solution (Aldrich) was applied to an electrochemical cell and left for up to 7 min while (a) no potential or (b) +2.0 V vs. Ag—AgCl was applied. The cell was then rinsed with deionised water and dried. Ferricyanide solution as described in Example 7 or ruthenium hexaamine solution consisting of 10 mM $[Ru(NH_3)_6]Cl_3$ (Alfa Aesar) in Tris pH 9 buffer (Sigma) with 100 mM KCl (BDH), 50 mM $MgSO_4$ (Sigma) and 1% sodium taurocholate (Sigma) was then deposited in the cell and a cyclic voltammogram recorded at 100 mVs$^{-1}$. The experiment was repeated using saturated aqueous sodium carbonate solution instead of Tyrode's solution.

Figure 16:
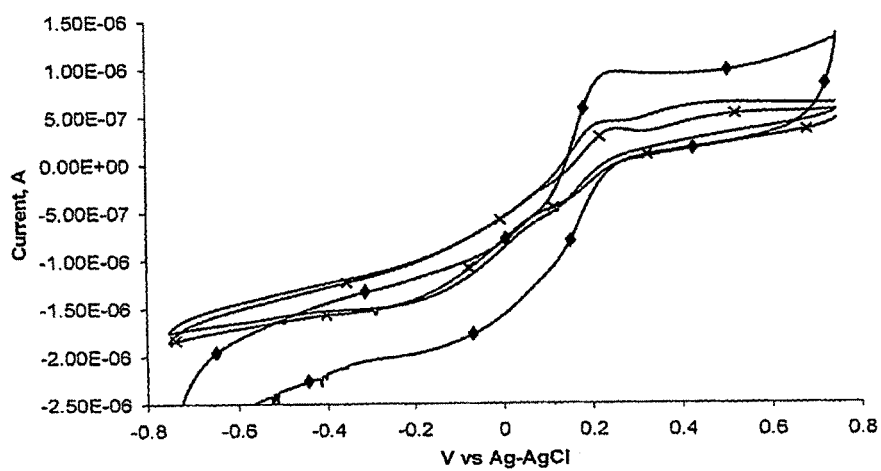
FIG. 16 shows the effect of application of potential step in the presence of Tyrode's solution prior to completing cyclic voltammetry, comparing voltammograms completed (a) without pretreatment of electrodes (solid line), (b) after exposure to Tyrode's solution for 7 minutes (crosses) and (c) after pretreatment by application of 2.0V for 30 seconds in the presence of Tyrode's solution (diamonds)
Figure 17:
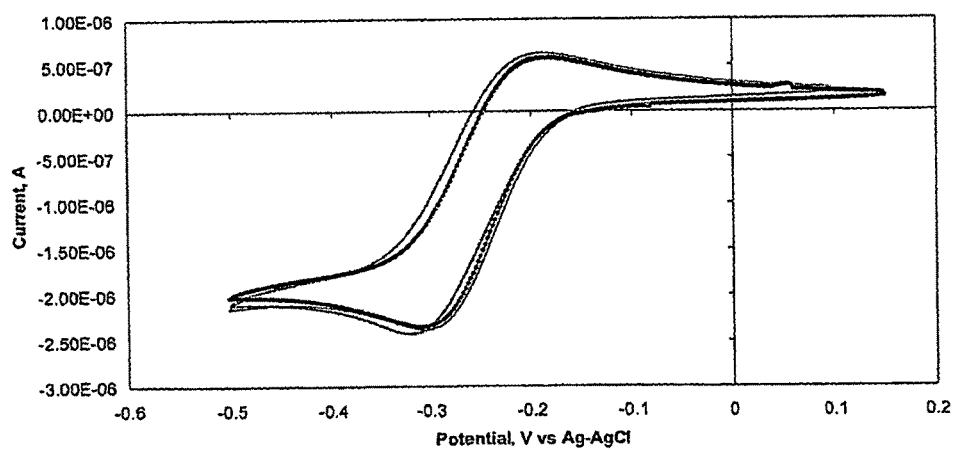
FIG. 17 shows the effect of application of potential step in the presence of sodium carbonate (solid black), compared with soaking for 7 minutes in a solution of Tyrode's (diamonds), compared with no electrode pretreatment (solid grey)

The results for the ferricyanide experiments are depicted in FIG. 16, where the solid line shows no pre-treatment, the crosses show pre-treatment with Tyrode's solution for 7 minutes but no application of potential and the diamonds show pre-treatment by application of a potential in the presence of Tyrode's solution. The results for the ruthenium hexaamine experiments are depicted in FIG. 17, where the solid grey line shows the result of no pre-treatment, the diamonds show the results of soaking in Tyrode's solution and the solid black line shows sodium carbonate pretreatment with application of a +2.0 V vs. AgAgCl potential step for a 30 second duration.

Example 9

Pretreatment Using Hydrogen Peroxide

Figure 18:
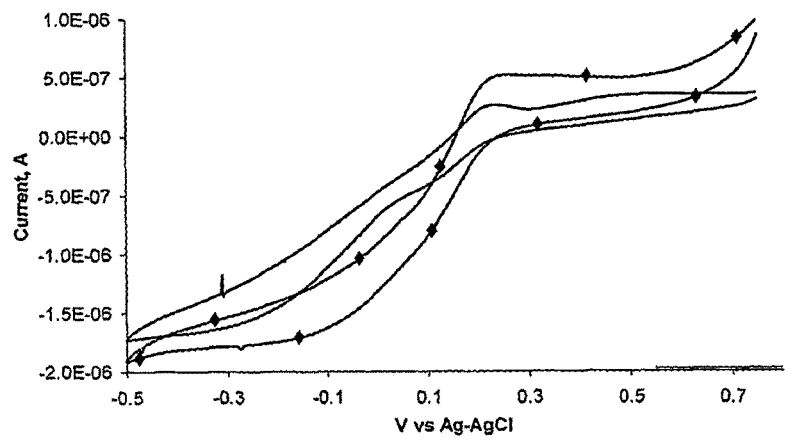
FIG. 18 shows the effect of application of a potential step in the presence of hydrogen peroxide prior to recording cyclic voltammograms in ferricyanide, comparing voltammograms completed without pre-treatment (solid black line), with those completed after peroxide pretreatment at 2.0V for 4 minutes (diamonds)

Hydrogen peroxide (Aldrich) was applied to an electrochemical cell and left for up to 9 min while (a) no potential or (b) +2.0 V vs Ag—AgCl was applied for 4 minutes. The cell was then rinsed with deionised water and dried. Ferricyanide-solution as described in Example 7 was then deposited in the cell and a cyclic voltammogram recorded at 100 mVs$^{-1}$. The results are shown in FIG. 18, where a solid black line shows the result of no pre-treatment step, and the diamonds show the results of pre-treatment in the presence of hydrogen peroxide.

Example 10

Pretreatment Using Linear Sweep

Figure 19:
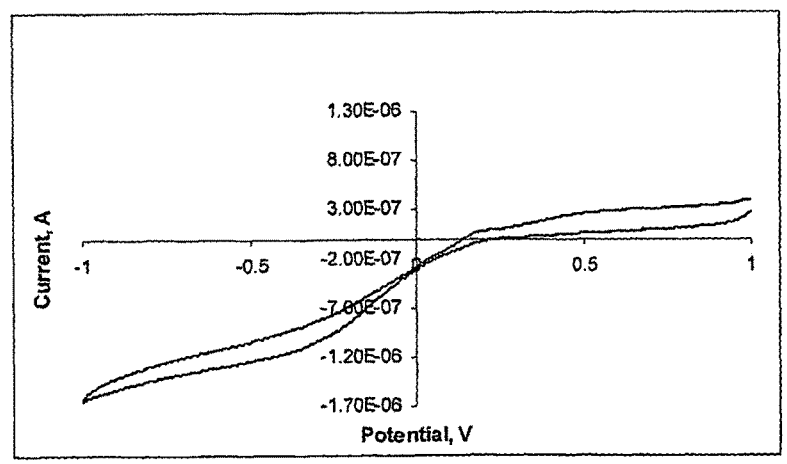
FIG. 19 depicts a ferricyanide voltammetric response of a sensor which has not been pre-treated.
Figure 20A:
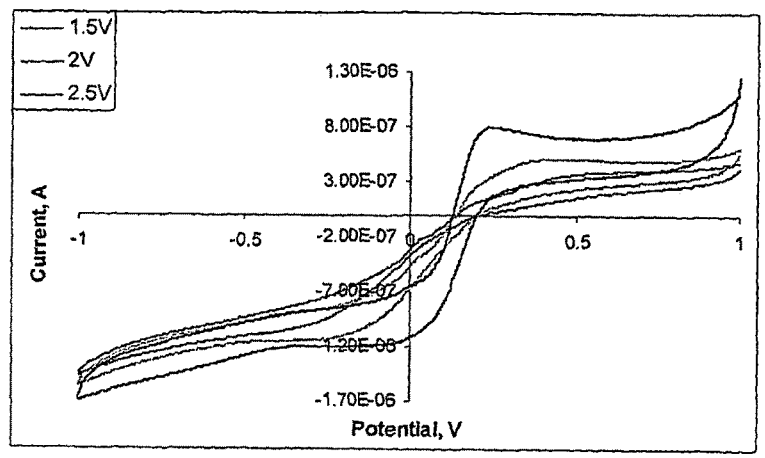
FIG. 20a shows the corresponding voltammetric response after electrochemical pretreatment.
Figure 20B:
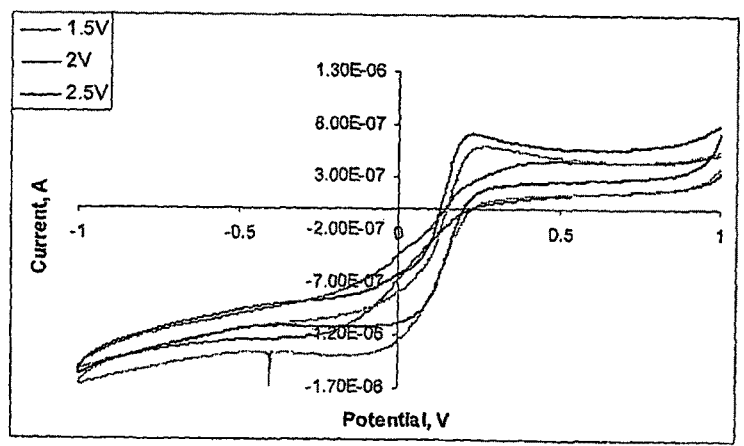
FIG. 20b shows the corresponding voltammetric response after electrochemical pretreatment in the presence of sodium carbonate.

Electrochemical cells were pre-treated using a linear sweep of potential from 0V up to one of the following potentials: 1.5V, 2V and 2.5V. Pre-treatment was carried out either in a ferricyanide solution as described in Example 7 or in saturated sodium carbonate solution. Subsequently, cyclic voltammograms were completed at 200 mV s$^{-1}$ in the ferricyanide solution. FIG. 19 shows the result where no pre-treatment is carried out, whilst FIGS. 20a and b show the results of pre-treating in ferricyanide and sodium carbonate respectively.

Example 11

Electrochemical Potential Pre-Treatment Prior to Sensor Testing

A device of the type described in Example 4 was used, the device having a receptacle containing reagents for a total cholesterol test as described in Example 4, except that the cis-isomer of the ruthenium complex as detailed in GB0611800.4 was used in the place of ruthenium hexaamine. The reagents were freeze dried. The device was pretreated and used to test for the total cholesterol (TC) content of plasma samples.

Figure 21:
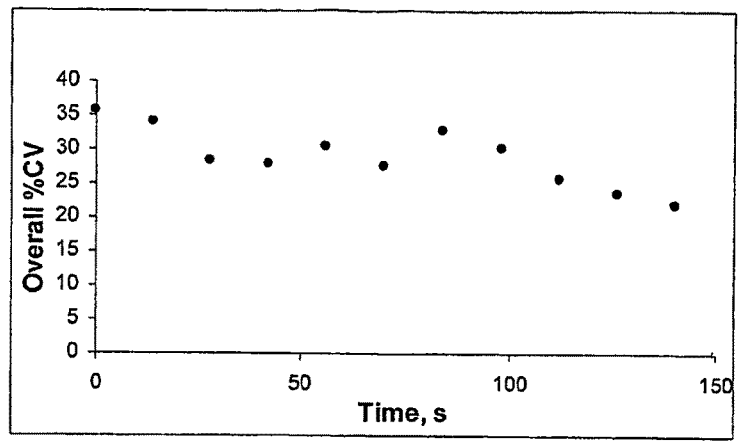
FIGS. 21 to 23 show the effect of a 0V, 1.5V and 2.5V potential step respectively, applied prior to carrying out a sensor test.
Figure 22:
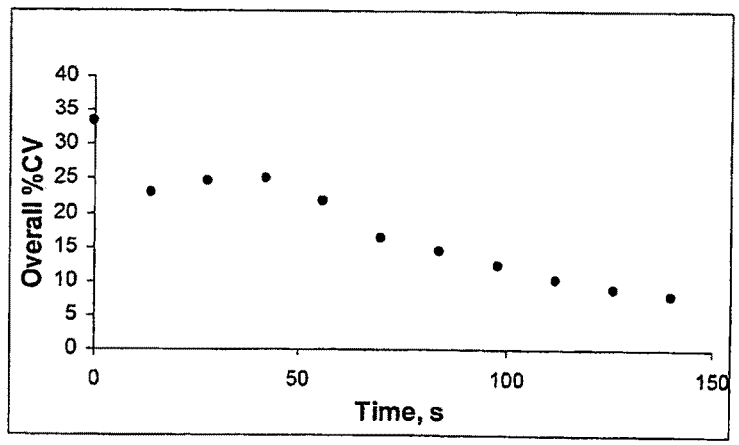
Figure 23:
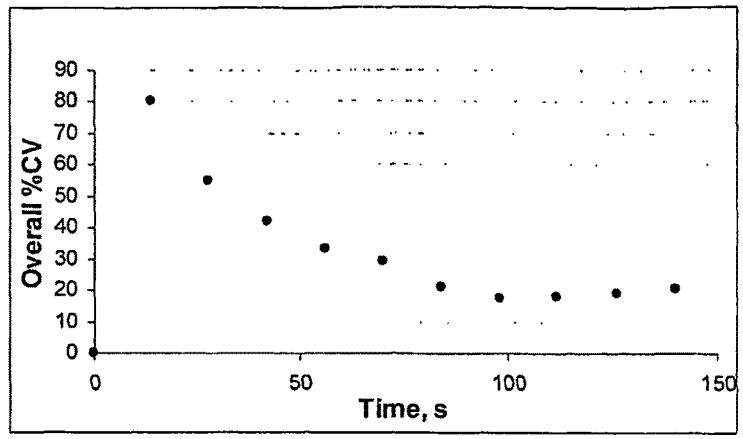

Pretreatment was carried out by application of an electrochemical potential for one second per cell, applied immediately upon application of plasma to the sensor using a multiplexer (MX452, Sternhagen Design) attached to an Autolab (PGSTAT 12) and GPES software v4.9.005. A five second delay followed, after which the oxidation current was measured at 0.15V at 11 time points (0, 14, 28, 42, 56, 70, 84, 98, 112, 126 and 140 seconds), with a reduction current measured at −0.45V at 141 seconds. Testing was completed over a clinically significant range of total cholesterol concentrations as given in Table 3. Three different pre-treatment potentials were compared: 0V, 1.5V and 2.5V. Three repeats were conducted per sample per pre-treatment potential and the results are depicted in FIGS. 21, 22 and 23 for 0V, 1.5V and 2.5V pre-treatment respectively.

TABLE 3

| [TC], mM |
| --- |
| 7.45 |
| 2.49 |
| 4.99 |

Example 12

Sodium Carbonate Pretreatment

An experiment was conducted to measure, by chronoamperometry, the response of ferrocyanide generated biochemically from an enzyme catalysed electrochemical reaction between ferricyanide and nicotinamide adenine dinucleotide (NADH). Two solutions of ferricyanide solution comprising 25 mM $K_3[Fe(CN)_6]$ (Aldrich) in Tris pH 9 buffer (Sigma) with 100 mM KCl (BDH), 50 mM $MgSO_4$ (Sigma) and 1% sodium taurocholate (Sigma) were prepared. To one solution, Putidaredoxin reductase (PdR) was added and to the other diaphorase was added (both were used at a concentration of 5 $mgml^{-1}$). NADH solutions were prepared at the following concentrations: 7, 5, 3, 2 and 1 mM in Tris pH 9 buffer (Sigma) with 100 mM KCl (BDH), 50 mM $MgSO_4$ (Sigma) and 1% sodium taurocholate (Sigma).

An electrochemical cell was prepared by pre-treating in a solution of sodium carbonate by application of a 2V potential for 30 seconds. A second cell was not pre-treated. 20 μl of a 1:1 mixture of the PdR ferricyanide solution and the 7 mM NADH solution were applied to each electrochemical cell. Fifteen seconds after adding the solutions, the oxidation current was measured at 0.15V at 11 time points (0, 14, 28, 42, 56, 70, 84, 98, 112, 126 and 140 seconds), with a reduction current measured at −0.45V at 141 seconds. In the case of the non-pretreated cell, a 0V (one second per cell) step was added to the beginning of the chronoamperometry program. The experiment was repeated three times.

Figure 24:
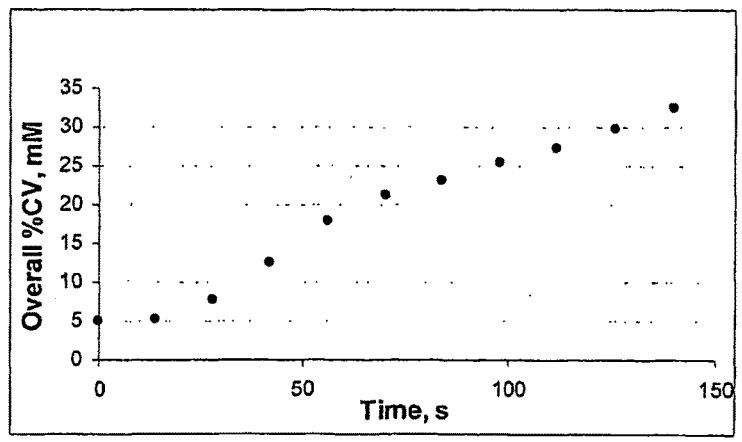
FIG. 24 shows the effect of sodium carbonate pretreatment on a biosensor comprising diaphorase.
Figure 25:
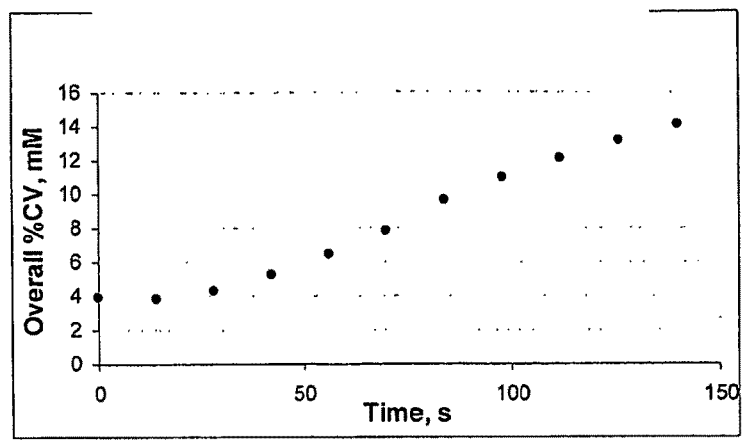
FIG. 25 shows the effect of sodium carbonate pretreatment on a biosensor comprising Putidaredoxin reductase.

Similar sets of results were obtained using 1:1 mixtures of the PdR ferricyanide solution and the other concentrations of NADH solutions, and using the diaphorase ferricyanide solution combined with each NADH solution. The % CV was calculated for each time point (averaging over all NADH concentrations) and the results are shown in FIGS. 24 (diaphorase) and 25 (putidaredoxin reductase).

Example 13

Laser Pre-Treatment

All tests were carried out using a device having 4 receptacles of the type depicted in FIG. 1 of WO 2006/000828.

A film of 250 μm PET was printed with a conductive carbon ink in a pattern that defines the working electrode and conductive tracks. This was then dried at 100° C. The carbon ink print was subsequently over printed with a dielectric ink, except for the part of the tracks that were required to mate with a connector in a measuring instrument, where over printing was not carried out. The dielectric ink was then dried at 100° C. Two further coats of dielectric ink were applied and each was dried at 100° C.

Four holes having a 1 mm diameter were then formed in the film by laser drilling for 2.5 seconds, using a pulsed $ND:YVO_4$ laser operating at a wavelength of 266 nm, a pulse rate frequency (prf) of 25 kHz and a trepan speed of 120 kHz (1800 r.p.m). The film was then adhered to a base layer of Pall Versapor porous membrane using adhesive tape, thus creating four wells. An Ag/AgCl pseudo reference electrode was used.

An aqueous solution of $Ru(NH_3)_6Cl_3$ was then applied to the devices produced as described above. A five second period was allowed to lapse prior to application of a potential. Next, a potential of −0.45V was applied to each cell simultaneously and after 1 second, the current of each cell was measured sequentially.

Figure 26:
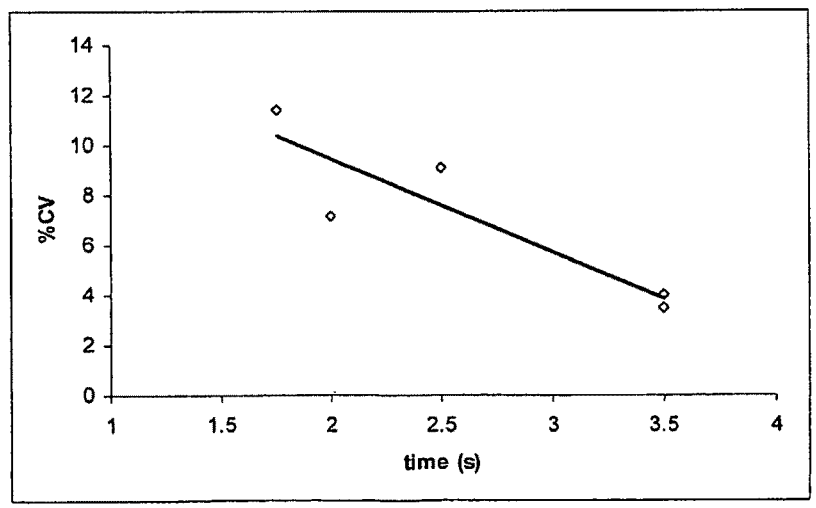
FIG. 26 shows the decrease in % CV with increasing laser treatment application time.

This series of experiments was repeated using devices produced using a variety of different laser operating times ("laser on"), as set out in Table 4 below. For each series of results, the coefficient of variation (CV) was determined. FIG. 26 plots the resulting CV values against the time during which the laser was applied.

TABLE 4

| Trepan speed (KHz) | Trepan speed (r.p.m) | PRF(KHz) | laser on t(s) | % CV |
| --- | --- | --- | --- | --- |
| 120 | 1800 | 25 | 2.5 | 9.09 |
| 120 | 1800 | 25 | 3.5 | 3.51 |
| 120 | 1800 | 25 | 1.75 | 11.44 |
| 120 | 1800 | 25 | 2 | 7.18 |
| 120 | 1800 | 25 | 3.5 | 3.97 |

The invention claimed is:

1. A method of preparing an electrochemical device, said method comprising:
   (a) providing an electrochemical cell having a working electrode and a pseudo reference electrode;
   (b) preconditioning the working electrode by applying a stepped preconditioning potential across the cell for a duration of up to 100s, wherein the preconditioning potential is applied in the presence of an aqueous solution capable of allowing an electric current to pass and the preconditioning potential consists of either one potential step, or one positive and one negative potential step;
   (c) providing an electroactive reagent to the electrochemical cell and optionally drying the reagent;
   (d) supplying a sample comprising a bodily fluid to the device, the sample being in contact with the working electrode and with the electroactive reagent; and
   (e) applying a measuring potential across the cell and measuring the resulting electrochemical response;
   wherein the electrochemical response of the cell is not measured during the preconditioning step; and wherein said preconditioning step (b) is carried out either before step (c) or between steps (c) and (d).

2. A method according to claim 1, wherein the electroactive reagent comprises an electrochemical mediator.

3. A method according to claim 2, wherein the mediator is a ruthenium complex or a ferricyanide or ferrocyanide salt.

4. A method according to claim 1, wherein the electroactive reagent is substantially free of metals capable of adsorbing to the working electrode.

5. A method according to claim 1, wherein the electroactive reagent does not contain cobalt.

6. A method according to claim 1, wherein the preconditioning potential is applied in the presence of an aqueous buffer which contacts the working and pseudo reference electrodes.

7. A method according to claim 1, wherein the preconditioning potential is applied by stepping the potential to a value of between −0.1V and +1.8V.

8. A method according to claim 1, wherein the working electrode has at least one dimension of less than 50 μm.

9. A method according to claim 1, wherein the electrochemical cell is in the form of a receptacle, the working electrode is in a wall of the receptacle and the method comprises inserting the electroactive reagent into the receptacle.

10. A method according to claim 1, wherein the device comprises a strip having at least one receptacle or partial receptacle formed therein, the receptacle or partial receptacle having a first open part in a first surface of the strip to enable a sample to enter the receptacle or partial receptacle,
wherein the working electrode of the electrochemical cell is in a wall or walls of the receptacle or partial receptacle,
wherein the pseudo reference electrode of the electrochemical cell comprises a pseudo reference electrode layer formed on at least a part of the first surface of the strip, and
wherein the method comprises inserting the electroactive reagent into the receptacle.

11. A method according to claim 1, wherein the preconditioning potential is applied in the presence of an aqueous solution containing an anion which can be activated to form a per-derivative.

12. A method according to claim 1, wherein the preconditioning potential consists of a single potential step.

13. A method according to claim 1, wherein the preconditioning potential consists of one positive and one negative potential step.

14. A method according to claim 1, wherein said preconditioning step (b) is carried out before step (c).

15. A method of preparing an electrochemical device, said method comprising:
(a) providing an electrochemical cell having a working electrode and a pseudo reference electrode;
(b) treating the working electrode with a UV laser for a duration of at least 2s;
(c) providing an electroactive reagent to the electrochemical cell and optionally drying the reagent;
(d) supplying a sample comprising a bodily fluid to the device, the sample being in contact with the working electrode and with the electroactive reagent; and
(e) applying a measuring potential across the cell and measuring the resulting electrochemical response.

16. A method according to claim 15, wherein the electroactive reagent comprises an electrochemical mediator.

17. A method according to claim 16, wherein the mediator is a ruthenium complex or a ferricyanide or ferrocyanide salt.

18. A method according to claim 15, wherein the electroactive reagent is substantially free of metals capable of adsorbing to the working electrode.

19. A method according to claim 15, wherein the electroactive reagent does not contain cobalt.

20. A method according to claim 15, wherein the working electrode has at least one dimension of less than 50 μm.

21. A method according to claim 15, wherein the electrochemical cell is in the form of a receptacle, the working electrode is in a wall of the receptacle and the method comprises inserting the electroactive reagent into the receptacle.

22. A method according to claim 15, wherein the device comprises a strip having at least one receptacle or partial receptacle formed therein, the receptacle or partial receptacle having a first open part in a first surface of the strip to enable a sample to enter the receptacle or partial receptacle,
wherein the working electrode of the electrochemical cell is in a wall or walls of the receptacle or partial receptacle,
wherein the pseudo reference electrode of the electrochemical cell comprises a pseudo reference electrode layer formed on at least a part of the first surface of the strip, and
wherein the method comprises inserting the electroactive reagent into the receptacle.

23. A method according to claim 15, wherein the working electrode is preconditioned by applying a UV laser for a duration of at least 3s.

24. A method according to claim 15, wherein the working electrode is preconditioned by applying a pulsed UV laser operating at a pulse rate frequency (prf) of at least 25 kHz.

* * * * *

UNITED STATES PATENT AND TRADEMARK OFFICE
CERTIFICATE OF CORRECTION

PATENT NO. : 8,518,236 B2  
APPLICATION NO. : 11/993418  
DATED : August 27, 2013  
INVENTOR(S) : Patricia Mary Elizabeth Roblin, Mark Hyland and Christopher Paul Newman Page 1 of 1

It is certified that error appears in the above-identified patent and that said Letters Patent is hereby corrected as shown below:

In the Specification

In column 4, line 39, change "and a heating" to --and IR heating--.

In column 11, line 37, change "walks)" to --wall(s)--.

In column 15, line 12, change "(ChB)" to --(ChE)--.

In column 15, line 50, change "HUBS" to --HEPBS--.

In column 17, line 43, change "Stemhagen" to --Sternhagen--.

Signed and Sealed this  
Fifth Day of November, 2013

Teresa Stanek Rea  
*Deputy Director of the United States Patent and Trademark Office*